(12) United States Patent
Johnson

(10) Patent No.: US 11,751,799 B1
(45) Date of Patent: Sep. 12, 2023

(54) METHODS AND SYSTEMS FOR DIAGNOSING COGNITIVE CONDITIONS

(71) Applicant: Lanny Leo Johnson, Henderson, NV (US)

(72) Inventor: Lanny Leo Johnson, Henderson, NV (US)

(*) Notice: Subject to any disclaimer, the term of this patent is extended or adjusted under 35 U.S.C. 154(b) by 0 days.

(21) Appl. No.: 18/166,359

(22) Filed: Feb. 8, 2023

(51) Int. Cl.
*A61B 5/00* (2006.01)
*A61B 5/11* (2006.01)

(52) U.S. Cl.
CPC ............. *A61B 5/4088* (2013.01); *A61B 5/11* (2013.01); *A61B 5/4824* (2013.01); *A61B 2562/028* (2013.01); *A61B 2562/0219* (2013.01)

(58) Field of Classification Search
CPC ....... A61B 5/4088; A61B 5/11; A61B 5/4824; A61B 2562/0219; A61B 2562/028
See application file for complete search history.

(56) References Cited

U.S. PATENT DOCUMENTS

| | | | | |
|---|---|---|---|---|
| 8,833,178 B2* | 9/2014 | de Boissieu | ............ | G01L 5/162 73/862.043 |
| 9,080,854 B2* | 7/2015 | De Boissieu | ............ | G01B 5/28 |
| 9,443,409 B1* | 9/2016 | Hyde | ............ | A61B 5/11 |
| 10,722,165 B1* | 7/2020 | Douglas | ............ | A61B 5/163 |
| 10,758,732 B1* | 9/2020 | Heldman | ............ | A61B 5/291 |
| 10,939,821 B2* | 3/2021 | Yaghi | ............ | A61B 5/163 |
| 11,276,498 B2* | 3/2022 | Schler | ............ | A61B 5/4088 |
| 11,424,031 B2* | 8/2022 | Baker | ............ | G16H 10/20 |
| 2007/0135735 A1* | 6/2007 | Ellis | ............ | A61B 90/06 600/587 |
| 2009/0024050 A1* | 1/2009 | Jung | ............ | A61B 5/4064 600/544 |
| 2009/0306741 A1* | 12/2009 | Hogle | ............ | A61N 1/36103 600/595 |
| 2009/0312817 A1* | 12/2009 | Hogle | ............ | A61B 5/682 607/54 |
| 2014/0143692 A1* | 5/2014 | Wigdor | ............ | G06F 9/451 715/764 |
| 2015/0050626 A1* | 2/2015 | Tully | ............ | A61B 5/16 434/236 |

(Continued)

OTHER PUBLICATIONS

Application of tactile memory examination as an option to visual- and verbal-based batteries, published Sep. 2021 (Year: 2021).*

(Continued)

*Primary Examiner* — May A Abouelela
(74) *Attorney, Agent, or Firm* — Stonebridge IP, PLLC

(57) ABSTRACT

This disclosure provides methods for diagnosing a cognitive disorder including performing a tactile perception test on a subject, measuring the subject's tactile perception test performance with a microelectromechanical sensor, and performing a cognitive disorder diagnosis on the subject. The tactile perception test may include distinguishing between various shaped and sized objects and selecting a predetermined one. The tactile perception test may include a two-point discrimination test. The tactile perception test may include testing lower extremity coordination. The tactile perception test may include testing upper extremity coordination. The cognitive disorder may include dementia, Alzheimer's, brain trauma, or concussion. The microelectromechanical sensor may include an accelerometer or gyroscope.

12 Claims, 15 Drawing Sheets

(56) References Cited

U.S. PATENT DOCUMENTS

| | | | |
|---|---|---|---|
| 2015/0208975 A1 | 7/2015 | Ghajar | |
| 2015/0294585 A1* | 10/2015 | Kullok | G09B 19/00 |
| | | | 434/236 |
| 2015/0294586 A1* | 10/2015 | Kullok | G09B 19/00 |
| | | | 434/236 |
| 2016/0091980 A1* | 3/2016 | Baranski | A61B 5/6824 |
| | | | 345/156 |
| 2016/0100788 A1* | 4/2016 | Sano | A61B 5/4094 |
| | | | 600/595 |
| 2017/0090569 A1* | 3/2017 | Levesque | G06F 21/36 |
| 2017/0258390 A1 | 9/2017 | Howard | |
| 2017/0296101 A1* | 10/2017 | Alberts | A61B 5/1116 |
| 2017/0323485 A1* | 11/2017 | Samec | A61B 5/024 |
| 2018/0360368 A1* | 12/2018 | Gatto | A61B 5/14532 |
| 2019/0043322 A1* | 2/2019 | Tachi | G06F 3/016 |
| 2019/0064927 A1* | 2/2019 | Tachi | G06F 3/01 |
| 2019/0328305 A1* | 10/2019 | Wood | A61B 5/40 |
| 2020/0042323 A1* | 2/2020 | Sano | G06F 9/30094 |
| 2020/0077892 A1* | 3/2020 | Tran | G08B 21/0492 |
| 2020/0179374 A1* | 6/2020 | Orefice | A61K 31/36 |
| 2020/0388287 A1* | 12/2020 | Anushiravani | A61B 5/4815 |
| 2020/0405215 A1* | 12/2020 | Tinjust | A61B 5/7405 |
| 2021/0169417 A1* | 6/2021 | Burton | A61B 5/4857 |
| 2021/0322772 A1* | 10/2021 | Ramos De Miguel | |
| | | | A61N 1/36036 |
| 2022/0071535 A1* | 3/2022 | Jernigan | A61B 5/11 |
| 2022/0079444 A1* | 3/2022 | Kahl | A61B 5/1101 |
| 2022/0125315 A1* | 4/2022 | Olde | A61B 5/4005 |
| 2022/0142535 A1* | 5/2022 | Burstein | A61B 5/441 |
| 2022/0248980 A1* | 8/2022 | Devani | A61B 5/1126 |
| 2022/0346699 A1* | 11/2022 | Lipsmeier | A61B 5/746 |
| 2022/0351824 A1* | 11/2022 | Weissberger | G16H 50/30 |
| 2022/0374080 A1* | 11/2022 | Lee | G06F 3/016 |
| 2023/0010314 A1* | 1/2023 | Vegar | A61B 5/14507 |

OTHER PUBLICATIONS

Craig et al., "Identification of scanned and static tactile patterns", Percept. Psychophys. 2002,64 (1), 107-120.

D. R. Fregoso et al., "Skin-brain axis signaling mediates behavioral changes after skin wounding", Brain, Behavior, & Immunity—Health, vol. 15, 2021, 100279.

Dabbous et al., "Artificial Bio-Inspired Tactile Receptive Fields for Edge Orientation Classification," 2021 IEEE International Symposium on Circuits and Systems (ISCAS), 2021, pp. 1-5.

Eggenberger et al., "Body Temperature Is Associated With Cognitive Performance in Older Adults With and Without Mild Cognitive Impairment: A Cross-sectional Analysis", Sec. Neurocognitive Aging and Behavior, Frontiers in Aging Neuroscience, Feb. 12, 2021;13:585904.

Hay et al., "Orientation processing by synaptic integration across first-order tactile neurons", PLOS Published: Dec. 2, 2020.

Igase et al., "Skin Autofluorescence Examination as a Diagnostic Tool for Mild Cognitive Impairment in Healthy People", J. Alzheimers Dis., 2017;55(4) :1481-1487.

Johnson et al., "The roles and functions of cutaneous mechanoreceptors", Curr. Opin. Neurobiol. 2011, 455-461.

Lederman et al., "Hand movements: A window into haptic object recognition", Cognitive Psychol. 19, 342-368 (1987).

Mastrogiannis et al., Abstract, "Correlation of Cognitive Status With Impaired Skin Microvascular Reactivity in Newly Diagnosed Untreated Hypertensives," Journal of Hypertension, 40(Suppl 1):p. e265, Jun. 2022.

McDonald at al., "Neuromorphic Tactile Edge Orientation Classification in an Unsupervised Spiking Neural Network", Sensors 2022, 22(18), 6998.

Nakatani et al., "Temporal coherency of mechanical stimuli modulates tactile form perception", Sci Rep 11, 11737 (2021).

Pruszynski et al., "A Rapid Tactile-Motor Reflex Automatically Guides Reaching toward Handheld Objects", Current Biology 26, 788-792, Mar. 21, 2016.

Pruszynski et al., "Edge-orientation processing in first-order tactile neurons," Nat Neurosci., Oct. 2014; 17(10):1404-9.

Pruszynski et al., "Fast and accurate edge orientation processing during object manipulation", eLife 2018;7:e31200.

Pruszynski et al., "Primary motor cortex underlies multi-joint integration for fast feedback control", Nature; 478(7369): 387-390.

Weiler et al., "Spinal stretch reflexes support efficient hand control", Nat Neurosci., 22, 529-533 (2019).

Wen et al., "The link between cutaneous inflammation and cognitive impairment", JEADV, first published: Jun. 24, 2022.

Wikipedia, "Proprioception", the free encyclopedia, last edited on Jan. 2, 2023.

Wikipedia, "Two-point discrimination", the free encyclopedia, last edited on Nov. 1, 2022.

Wikipedia, "Cognitive disorder", the free encyclopedia.

Zhang et al., "The Relationship Between Alzheimer's Disease and Skin Diseases: A Review", Clin Cosmet Investig Dermatol., 2021;14:1551-1560.

Mendez et aL., "Skin conduction levels differentiate frontotemporal dementia from alzheimer's desease", J Neuropsychiatry Clin Neurosci., 2018; 3(03): 208-213.

* cited by examiner

METHODS AND SYSTEMS FOR DIAGNOSING COGNITIVE CONDITIONS

BACKGROUND

Technical Field of the Invention

The present disclosure relates to a system and methods for diagnosing and/or evaluating cognitive conditions. In particular, the present disclosure relates to a method and a system to assess cognitive impairment and disorders based on performing and analyzing one or more cognitive stimulus/response tests with microelectromechanical system (MEMS) technology.

Description of the Related Art

Cognitive disorders have become increasingly important as humanity ages and collision sports continue to grow in popularity. As society waits for a definite treatment for Alzheimer's disease and dementia, there continues to be a need for clear identification and diagnosis, in particular, hoping for early diagnoses when and if treatable. Presently there is a need for prognostic determination throughout the rehabilitation process.

The traumatic brain syndrome problem has come front and center due to collision sports. Most notable has been the tragic long-term consequences of those who played professional football, boxing, and mixed martial arts. However, less publicized are the brain injuries in youth and amateur sports; i.e., soccer for instance. In addition, there are other causes; i.e. auto accidents, slip and fall, violent attacks, and warrior injuries. Much attention has been given to the differential diagnosis and the treatment of cognitive disease, yet the art is still in the formative state. Metrics for rehabilitation are under study. The recovery metrics have become important, for example, concerning the return of a player to competition, especially in the National Football League.

Beyond the obvious signs and symptoms of being forgetful, confused, and finally the failure to orient to person, place or time there is a significant need for more sensitive, specific and reliable means of diagnosing cognitive disorders for Alzheimer's disease and dementia.

Among the many methods proposed to evaluate cognitive disorders the sensibility of the skin as a means of assessment has been overlooked, especially the role of tactile edge orientation processing. There are publications related to skin disease and/or injury, and brain disease, but none related to tactile edge orientation processing as a diagnostic method or included in a system for medical diagnosis.

Wearable devices are common to all measurements of motion and have been used to correlate body temperature with cognitive disease diagnosis, but not those measuring fine psychomotor function in cognitive disease. The microcirculation of the skin has been correlated with cognitive disorders, but not tactile edge orientation processing (TEOP). Skin conductance levels have been used to differentiate cognitive disorders as a subject's skin's response to various visual television imaging, but not fine psychomotor functioning.

State-of-the-art methods of diagnosing and assessing these various cognitive conditions are time consuming, expensive, and/or mostly unreliable. Moreover, conventional techniques have significant variability from clinician to clinician because they are subject to observational and recording variation by the health care providers.

The present invention addresses the shortcomings described above and improves the medical diagnosis of cognitive conditions by providing comprehensive, sensitive, specific, reliable, and reproducible means in diagnosing cognitive conditions including collected data storage for subsequent review.

SUMMARY DISCLOSURE OF THE INVENTION

This disclosure provides methods for diagnosing a cognitive disorder including performing a tactile perception test on a subject, measuring the subject's tactile perception test performance with a microelectromechanical sensor, and performing a cognitive disorder diagnosis on the subject. The tactile perception test may include distinguishing between various shaped and sized objects and selecting a predetermined one. The tactile perception test may include a two-point discrimination test. The tactile perception test may include testing lower extremity coordination. The tactile perception test may include testing upper extremity coordination. The cognitive disorder may include dementia, Alzheimer's, brain trauma, or concussion. The microelectromechanical sensor may include an accelerometer or gyroscope.

Accordingly, systems and methods that diagnose cognitive conditions are disclosed. The methods include monitoring at least one sensor attached on at least one body part of a subject, the at least one sensor configured to detect motions of the at least one body part and transmit kinematic data to a signature comparing device. The method includes providing instructions to the subject to instruct the subject to perform a task. The signature comparing device compares a subject's composite signatures based on the kinematic data to normal composite signatures to evaluate differences between the subject's observed signature and the subject's normal signature. When the difference is larger than a pre-determined threshold, the method identifies the subject as having a cognitive condition. When the difference is smaller than a pre-determined threshold, the method identifies the subject as not having a cognitive condition.

Other features and aspects will be apparent from the following detailed description, the drawings, and the claims.

BRIEF DESCRIPTION OF THE DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DISCLOSURE OF THE INVENTION

Figure 1:
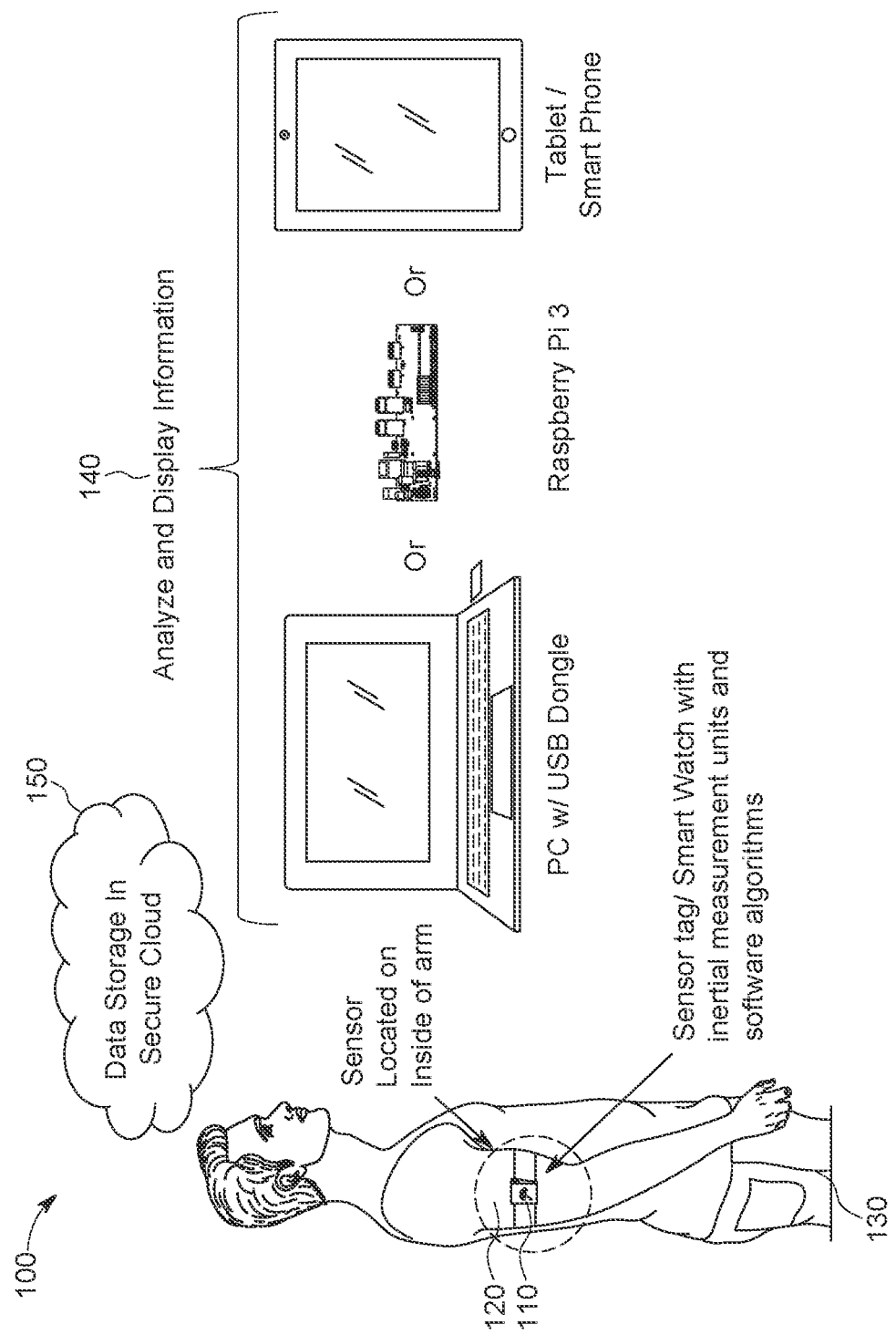
FIG. 1 is a schematic diagram of a system for dynamic diagnosis of cognitive conditions.

The disclosed systems and methods will now be described in detail hereinafter with reference to the accompanied drawings, which form a part of the present application, and which show, by way of illustration, specific examples or embodiments. Please note that the systems and methods may, however, be embodied in a variety of different forms and, therefore, the covered or claimed subject matter is intended to be construed as not being limited to any of the embodiments to be set forth below. Please also note that the disclosure may be embodied as methods, devices, components, or systems. Accordingly, embodiments of the disclosed system and methods may, for example, take the form of hardware, software, firmware, or any combination thereof.

Throughout the specification and claims, terms may have nuanced meanings suggested or implied in context beyond an explicitly stated meaning. Likewise, the phrase "in one embodiment" or "in some embodiments" as used herein does not necessarily refer to the same embodiment and the phrase "in another embodiment" or "in other embodiments" as used herein does not necessarily refer to a different embodiment. It is intended, for example, that claimed subject matter may include combinations of exemplary embodiments in whole or in part. Moreover, the phrase "in one implementation", "in another implementation", or "in some implementations" as used herein does not necessarily refer to the same implementation or different implementation. It is intended, for example, that claimed subject matter may include combinations of the disclosed features from the implementations in whole or in part.

In general, terminology may be understood at least in part from usage in context. For example, terms, such as "and", "or", or "and/or," as used herein may include a variety of meanings that may depend at least in part upon the context in which such terms are used. In addition, the term "one or more" or "at least one" as used herein, depending at least in part upon context, may be used to describe any feature, structure, or characteristic in a singular sense or may be used to describe combinations of features, structures, or characteristics in a plural sense. Similarly, terms, such as "a", "an", or "the", again, may be understood to convey a singular usage or to convey a plural usage, depending at least in part upon context. In addition, the term "based on" or "determined by" may be understood as not necessarily intended to convey an exclusive set of factors and may, instead, allow for existence of additional factors not necessarily expressly described, again, depending at least in part on context.

MODES FOR CARRYING OUT THE INVENTION

This invention provides novel clinical tests for the evaluation of cognitive conditions. The cognitive conditions includes but are not limited to, brain trauma, concussions, dementia, Alzheimer's, inebriation, etc. MEMS sensors and/or synchronized video can be used to evaluate the subject's response to the tests. The use of sensors and video removes clinical human judgement which is subject to observational and recording variations by healthcare professionals. The invention thus provides accurate diagnoses of cognitive conditions that can be determined through objective MEMS sensors and computer algorithms. Sensors are very good at determining subtle differences in performance that cannot be picked up by the human eye and in documenting the results. The inventive methods can thus also be administered by nonmedically trained people.

In embodiments, the evaluation can include four tests: (1) What is your first and last name, what city do you live in, what season is it?; (2)"What time is it?"; (3) TEOP (Tactile Edge Orientation Processing), e.g., reaching into a bag or the like and selecting a pre-designated object; and (4) Lower Extremity Leg Movement test.

The skin's tactile sensitivity plays a major role in collecting information thereby spontaneously reporting the body or body part's position in space. In addition, the sensibility of the skin spontaneously and intuitively collects information controlling proprioception. Proprioception, by definition, is the sense that lets us perceive the location, movement, and action of parts of the body. It encompasses a complex of sensations, including perception of joint position and movement, muscle force, and effort. Proprioception is the human inherent knowledge of the body parts position in space and the ability to control subsequent motion and position. Proprioception assessment, therefore, can be a significant factor in determining the cognitive status of a person.

Cognition assessment starts with determining the subject's orientation to person, place and time of year and or day. There are also additional factors that further define and or establish the person's cognitive status. The person must have the ability to pay attention or hear. They must understand communication accurately and fully. They must have the ability to properly respond to communication; i.e., simple instructions without delay in response time to instructions or commands. The person must have the ability to perform simple common tasks based upon their psychomotor integrity.

This invention provides the enlistment of human innate skin sensitivity data collection methods during performance of a well-defined non-visual assisted prescribed response to stimulus, for example, analogous to the 2-point discrimination test. The 2-point discrimination of various areas of the body that have known standards as to measuring the level of a certain area of the body's skin sensitivity. It is generally tested on the index finger's distal phalanx's volar pad. The normal human range is 2 to 4-millimeter separation of the pinpoint gauge on the finger. Other anatomical areas on the extremity or back may be as wide as 4-6 inches. This test has not been used for diagnosing human cognitive disorders.

Tactile edge orientation processing is generally not widely known and has not been used for assessment of cognitive disorders. The common denominators are the human's tactile edge orientation processing ability to distinguish between various shaped and sized objects and select a predetermined assigned one. The well-defined task is performed without visual assistance. The performance is solely dependent upon a subject's innate tactile edge orientation processing ability, known to require psychomotor coordination with the central nervous system.

Tactile edge orientation processing is a means of data collection with as little as a passive 1-millimeter depression in the skin of the thumb to enhance the psychomotor function and determination of extremity spatial relationships via enhanced proprioception. The extension of such is not only on the ipsilateral limb but perfectly controls the proprioception function of the contralateral upper extremity and hand.

Tactile edge orientation processing is a sensitive, specific, and reliable means of assessing psychomotor responses to physical impression of the skin. This method thus has application in assessment of psychomotor function related to cognitive disorders.

This method has application throughout the body. Tactile edge orientation processing is necessary for performing other psychomotor testing. For instance, the standard test for lower extremity coordination is the following: the process of rubbing one's heel up and down on the contralateral tibia requires the depression of the skin on the subject's heel coordinated with the perception of touching the skin anterior on the leg (that covering the anterior tibia). This task performance includes the coordination of skin sensitivity of both anatomical areas transmitting information to the psychomotor system for performance and coordination. Even small side to side and up and down position of the contralateral heel on the other leg can be perceived and is sensitive to location, speed, and acceleration.

Sensation perceived in one's hand is sent to and from the central nervous system to control psychomotor responses. There is, however, some reception and response in the spinal cord area and back which influences proprioception, yet still requires central nervous system input.

In addition, complex coordination of the upper extremity of humans and monkeys goes through processing in the cerebral cortex. Normal skin perception plays a major role in measuring and establishing one's cognition by a psychomotor response. This is also true for the classic index finger to the nose test that success requires confirmation of the touch of the finger skin to the skin of the nose.

Tactile palpation of an object that is independently moving is subject to perception and grasp similar to when the person had visually seen the change in position. This supports the inherent function to be normal for person seeking to grasp an intended object otherwise blinded to them. This is implemented in the present methods of assessing cognitive function. The methods are within the human ability to successfully perform; e.g., the identification and selection of loose objects in a container not otherwise visualized.

Humans have normal capacity to be accurate and rapid in determining the nature of an object. This is important for the method of cognitive assessment provided herein. Not only skin displacement but also changes in skin displacement can produce tactile form perception. This supports the human ability to move the body part covered with skin to extract different pressures aiding perception of an object's shape, which is important for the methods on the invention. They also include skin perception aided by experiencing vibrations. The human hand can detect both form (geometric) and texture information of a contact surface. For example, surface geometry edges are detected when a tactile stimulus is presented on a finger pad. Human observers tend to actively scan the contact surface when they examine the surface texture roughness.

The above factors support the validity and expected standard results of the testing of cognitive conditions via the methods disclosed.

In addition to human evaluation with tactile edge orientation processing there is also the potential use of robots to accomplish similar tasks in artificial limbs. The disclosed methods of cognitive assessment have application in this context as well.

The present disclosure may diagnose cognitive conditions of a subject by performing one or more tests for diagnosing cognitive conditions with dispatch, in any setting without delay. Potential subjects for this cognitive testing may include athletes, warriors, or any subjects with or suspected with having any of a variety of cognitive clinical conditions. The cognitive clinical condition may include dementia, Alzheimer's, brain trauma, concussion, etc.

The methods can be performed by those with minimal technical skill. The diagnostic results may provide a permanent document for immediate report including comparisons to a normal cohort of the same or similar demographic. The method may include a means of comparison to prior tests on same subject to monitor progress of treatment and rehabilitation. In one implementation, the method may be used in sport concussion to determine whether or when the subject may be allowed to return to competition in sports.

The diagnosis may depend on analyzing a motion signature graphic of a subject when the subject is instructed to perform a task. The diagnosis may depend on one or more particular cognitive stimulus/response tests. In one implementation, a subject with cognitive disorders may move with tremors even at rest, and/or may often have interrupted motion when the subject activates their body part. In another implementation, a subject with cognitive disorders may even stop halfway and need repetition of provided instructions to compete a task. In another implementation, a subject with Parkinson's may become frozen at a certain position. In another implementation, a motion signature of a subject may include a graphic signature, which may be unique to the subject. The motion signature of the subject may be a replicable signature analogous to a person's autograph. In another implementation, a motion signature of a subject may include a tracing. The tracing may include a path, a pattern, and/or a graphic record.

In another implementation, there may be a commonality of signatures in normal and specific diseases and various stages. For example, a length and/or a breadth of the signature pattern for the clinically normal subjects may have a commonality, which may differ in a length and/or a breadth of the signature patterns of the specific disease conditions and various stages.

When sufficient data is collected, the signatures of normal subjects may have distinct and specific patterns. The distinct and specific patterns may be independent of the individual subjects producing the signatures. Having the distinct and specific patterns, the signatures of all normal subjects may appear similar. This may be referred as commonality of signatures for normal subjects.

When sufficient data is collected, the signatures of abnormal subjects with a pathological condition may have distinct and specific patterns. Each pathological condition may have the same signatures, no matter which subject is tested. There may be minimal variation in each subject, and there may be commonality of those with each specific diagnosis at the various stages of decline.

In another implementation, there may be commonality of signatures and or signature graphics for each different diagnosis and the stages thereof.

In another implementation, there may be commonality of signatures and or signature graphics at various clinical stages and/or severities of a specific disease.

The existing methods of diagnosing cognitive disorders lack a comprehensive means of accessing and simultaneously documenting the cognitive conditions. The early diagnosis of dementia, Alzheimer's and Parkinson's is difficult. This may be attributed that an existing test that includes psychomotor measurement performances lacks sufficient sensitivity. Some existing methods may include bio-markers, which may not access function. Thus, it may be difficult for conventional cognitive diagnostics to obtain early prediction of future likelihood of these conditions for family members. Sometimes, magnetic resonant imaging (MRI) methods do not correlate with functions in concussion, and may not predict the magnitude of the concussion, clues to treatment or prognosis of the concussion.

The present disclosure uses MEMS sensors to measure the movement during one or more tests for diagnosing cognitive conditions, and the MEMS sensors provide a high sensitivity level at a high rate in one or more degree of freedoms, for example, 1000 or more data points per second in accelerations, rotation, and angulations. The present disclosure provides a comprehensive means of documenting various cognitive conditions, for example but not limited to the standard various demographics, IQ, standard time, person, and place. In one implementation, the tests performed by using MEMS sensors may be used in conjunction with other modalities, for example but not limited to, MRI, to gain specific insights for diagnosing cognitive conditions of the subject.

The present disclosure describes one or more tests evaluating a test subject's proprioception. The proprioception tests measure the test subject's extremities in spatial location and the subject's control thereof.

The one or more tests for diagnosing cognitive conditions may include at least one of the tests of telling what time it is, a test of performing tactile edge orientation processing (TEOP), and a test of performing lower extremity leg movement.

In one implementation, a test of short-term memory may be performed at the conclusion of any other test for diagnosing cognitive conditions. In another implementation, the test of short-term memory may be performed at the conclusion of all other tests for diagnosing cognitive conditions.

Referring to FIG. 1, the present disclosure describes a system 100 for dynamic diagnosis of cognitive conditions. The system 100 may include a sensor or a set of sensors 110. A sensor attached to a body part 120 of a subject 130 may generate, sense, or otherwise measure kinematic data of a subject's body part.

The subject 130 may include a human being. The human being is used as an example to describe the disclosure and does not impose any limitation to the present disclosure. The subject's body part may be selected from a head, neck, shoulder, arm, elbow, forearm, wrist, hand, finger, spine, pelvis, hip, thigh, knee, leg, ankle, foot and toe.

The sensor transmits measured kinematic data during one or more tests for diagnosing cognitive conditions to one or more electronic devices 140 for further analyzing and processing. The data transmission may be either a wired transmission or a wireless transmission. The wireless transmission may include, for example and not limited to, Bluetooth, Bluetooth Low Energy (BLE), Zigbee, Z-Wave, 6LoWPAN, WI-FI or other wireless technology. The wireless communication may take place via radio frequency or ultrasound. The wireless communication may enable connection to cellular network via a smart phone or a computer enabled with WI-FI. Wireless sensing may be preferred to allow free movement of limbs and body. Short range wireless such as Bluetooth and Bluetooth Low Energy (BLE) may provide excellent battery life.

The one or more electronic devices 140 may include, as examples, a smart phone, a computer/laptop, a Raspberry Pi 3, or a tablet. The one or more electronic devices receives kinematic data from sensor 110. The one or more electronic devices 140 analyzes and processes the kinematic data using at least one algorithm and can report the results. The kinematic data may be multi-dimensional data, for example but not limited to, one or more spatial dimensions and one temporal (time) dimension. In one implementation, the results may be displayed in graphical form for the physician along with a suggestion for normal or abnormal classification. Abnormal classification may indicate an injury requiring surgical repair or cognitive therapy. In another implementation, the displayed result may be processed data, for example, a time interval between the starting of one test and the ending of the test.

Sensor 110 may also transmit the measured kinematic data to external data storage device 150 for data storage and/or further data processing. The data transmission may be either a wired transmission or a wireless transmission. External data storage device 150 may include an on-site data server, which may be in the same room or in the same building as the location of sensor 110 and the human being. In another implementation, external data storage device 150 may include an off-site on-line data storage device, for example and not limited to, a data cloud.

Optionally, electronic device 140 may transmit the processed data to external data storage device 150 for data storage and/or further data processing.

In one implementation, sensor 110 may include an accelerometer, so that sensor 110 attached to a body part 120 measures an acceleration of body part 120. When acceleration data from the accelerometer is analyzed as a function of time, a speed of body part 120 may be calculated given a known speed at a known time point. For example, the known speed of the body part at the known time point may be zero when the body part is in a resting state at the time point of zero.

The acceleration data from the accelerometer may be analyzed to provide speed data or position data. Integration of the acceleration data with respect to time can provide speed data for the accelerometer. Integration of the speed data with respect to time can provide position data for the accelerometer.

In some implementations, sensor 110 includes a gyroscope, so that the gyroscope attached to a body part measures rotational angles of the body part. The rotational angles may be represented by an x-axis rotational angle, a y-axis rotational angle, and a z-axis rotational angle. When rotational angle data from the gyroscope is analyzed as a function of time, a rotational speed of the body part may be calculated since the rotational speed is a time derivative of the rotational angle. Similarly, a rotational acceleration may be calculated as well since the rotational acceleration is a second-order time derivative of the rotational angle.

In some implementations, sensor 110 includes a magnetometer, so that the magnetometer attached to a body part measures direction or orientation of the body part. The direction or orientation of the body part may be represented by an angle relative to one particular direction, e.g., the north direction.

Sensor 110 may be a set of sensors including one or more accelerometer, one or more gyroscope, or one or more magnetometer. When the set of sensors is attached to a body part, acceleration data, rotational angle data, and/or orientation data of the body part may be simultaneously measured.

Sensor 110 may include one or more Micro Electro Mechanical System (MEMS) sensors. The MEMS sensor may be used to measure motion or locomotion of the subjects. Depending on specific pathological conditions of body part 120, the MEMS sensor may be properly assembled and tailored to the specific pathological conditions to provide a real time diagnosis of cognitive conditions and/or a real time diagnosis of various clinical stages thereof.

Sensor 110 may be used to measure composite motion of any muscle, tendon, and/or joint under any circumstances in free space. The exemplary implementations and embodiments described do not restrict motion measurement to a specific muscle, tendon, and or joint function. For example, MEMS sensors may be used to measure the position and motion of the human torso in activities of daily living.

In one embodiment, sensor 110 includes a set of individual sensors. The set of individual sensors may include a combination of miniature sensors. MEMS sensors may include components between 1 and 100 micrometers in size (e.g., 0.001 to 0.1 mm), and MEMS devices generally range in size from 20 micrometers to a millimeter (e.g., 0.02 to 1.0 mm).

Figure 2:
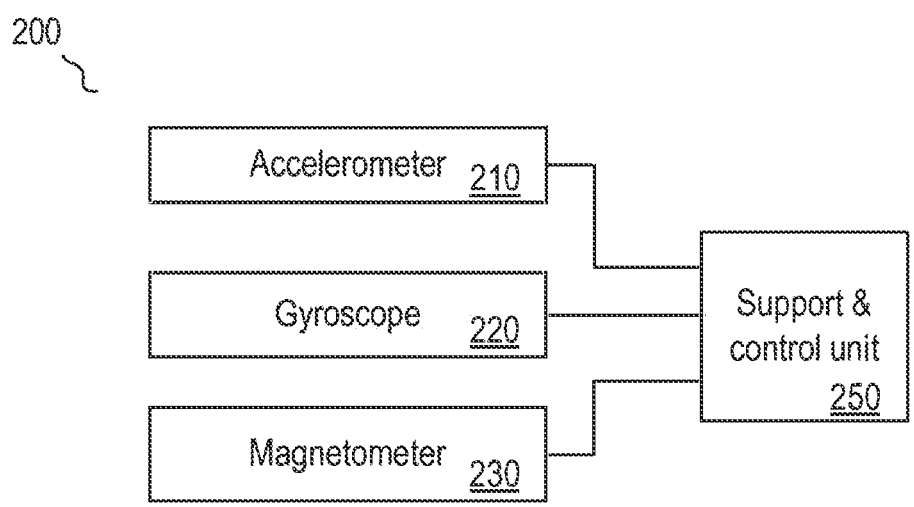
FIG. 2 is a schematic diagram of a sensor.

FIG. 2 shows an exemplary implementation of sensor 200 that includes 3-axis accelerometer 210, 3-axis gyroscope 220, and 3-axis magnetometer 230. Sensor 200 may include other supporting and/or control components (e.g., support & control unit 250), which may include but is not limited to any one or more of a microprocessor, memory, a wireless antenna, and a rechargeable battery. In one implementation, sensor 200 includes commercially available products and may be purchased off the shelf.

In one implementation, in addition to obtaining kinematic data, sensor 200 analyzes and processes the obtained kinematic data to generate at least one motion signature. For example, accelerometer 210 may obtain acceleration data as a function of time. The acceleration data may be transmitted to support & control unit 250. Support & control unit 250 analyzes and processes the acceleration data to generate motion signatures for accelerations, speeds, and/or positions of sensor 200. In a similar manner, support & control unit 250 analyzes and processes data from gyroscope 220 and magnetometer 230 to generate motion signatures for angular position, angular acceleration, angular velocity, orientation, change in orientation per unit time, and rate of change in orientation per unit time.

During diagnosis, the one or more MEMS sensors may be disposed on one or more body parts of the subject in a specific configuration. For example, a first MEMS sensor may be disposed at a first particular location of the body pat of the subject and a second sensor may be disposed at a second particular location of the same or different body part.

When, in response to receiving instructions, the subject preforms a task, the MEMS sensors generate kinematic data corresponding to motions of the one or more body parts of the subject. Based on the kinematic data, composite graphic signatures of the subject may be obtained and may be compared to normal composite signatures of normal subjects. A diagnosis result of the subject may be obtained based on a comparison between the composite signatures of the subject and the normal composite signatures. In another implementation, the system may obtain disease-specific composite signatures corresponding to a specific disease and compare the subject's composite signatures to the disease-specific composite signatures to determine whether a difference between the subject's composite signatures and the disease-specific composite signatures is larger than a disease-specific threshold. In response to the determination that the difference between the subject's composite signatures and the disease-specific composite signatures is not larger than the disease-specific threshold, the subject may be dragonized as to likely having the specific disease. In one implementation, the disease-specific threshold may be a pre-determined threshold for a group of subjects with similarly demographic background. In another implementation, the disease-specific threshold may be a pre-determined threshold unique to one or more subject. In another implementation, the subject's composite signatures may deviate from the disease-specific composite signatures wherein the deviation may be a large range from small deviation to large deviation. For example, the subject's composite signatures may deviate from the disease-specific composite signatures in timing and motion production.

The MEMS sensors may include but are not limited to, an accelerometer, gyroscope, magnetometer, and transceiver. The body part of the subject may include but is not limited to, a finger, hand, wrist, forearm, elbow, upper arm, shoulder, forehead, face, neck, chest, waist, abdomen, buttock, thigh, knee, shin, calf, ankle, heel, and toe. The composite signatures may include various motion and/or non-motion signatures, for example but not limited to, a speed, an acceleration, a position, a time duration, a range of motions, an interruption during motions, a tremor, a convulsion, and a spasticity. The cognitive conditions may be one or more types of diseases/prognoses, for example but not limited to, dementia, Alzheimer's, brain trauma, and concussion.

Figure 3:
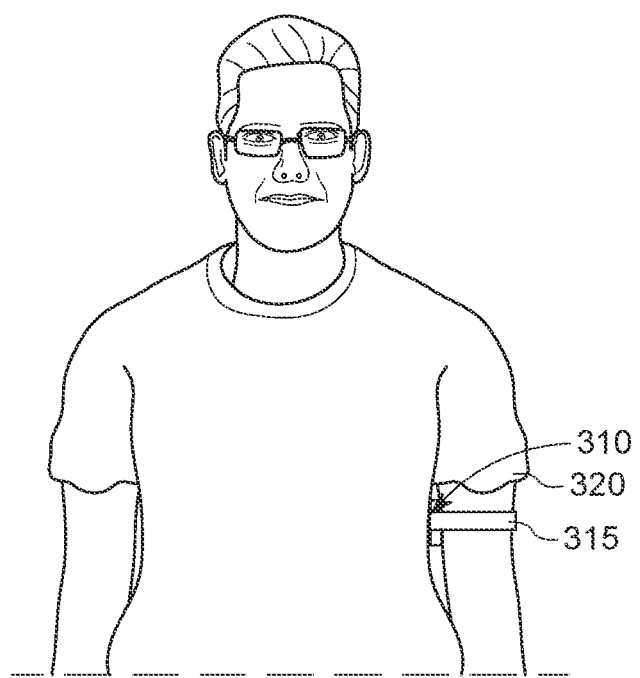
FIG. 3 is a schematic diagram of a location of the system.

Referring to FIG. 3, in one embodiment, sensor 310 fits in a recess between the bicep and triceps of the inner arm of arm 320. Sensor 310 may be attached to arm 320 by securing band 315. A portion of a housing of sensor 310 may have a triangular shape so that it may fit in the recess between the bicep and triceps of arm 320.

Sensor 320 may include a MEMS accelerometer, which may measure the acceleration of gravity in 3 axes to determine position of the arm from a known reference. Sensor 320 may include a MEMS gyroscope, which may measure the rotational angle to obtain the angular velocity. Optionally, sensor 320 may include a magnetometer, which generates magnetometer data.

The hardware to make these measurements may include a TI Sensor Tag, Apple Watch or any other off-the-self or custom device having a MEMS accelerometer and gyroscope with sufficient performance and within a short range of the wireless communications.

For each diagnosis, the corresponding tests may be pre-determined to include specific musculoskeletal motion patterns in case of associated paralysis; i.e. Parkinson's, stroke and or wounded warrior brain trauma. For example, they may be similar to when a supraspinatus injury is suspected, elevation in the scapular plane and external rotation with the arm at the side may be the most affected motion patterns. For elevation in the scapular plane, the tested motion pattern may include a starting position with the upper extremity hanging at the subject's side with the elbow extended, elevation to a maximal overhead position, and return to the starting position. For external rotation with the arm at the side, the tested motion pattern may include a starting position with the patient's palm of the hand resting on the umbilicus, external rotation to a maximally externally rotated position, and return to the starting position.

An acceleration of gravity in 3 axes relative to a known reference provides a signature of body part position during movement.

Figure 4:
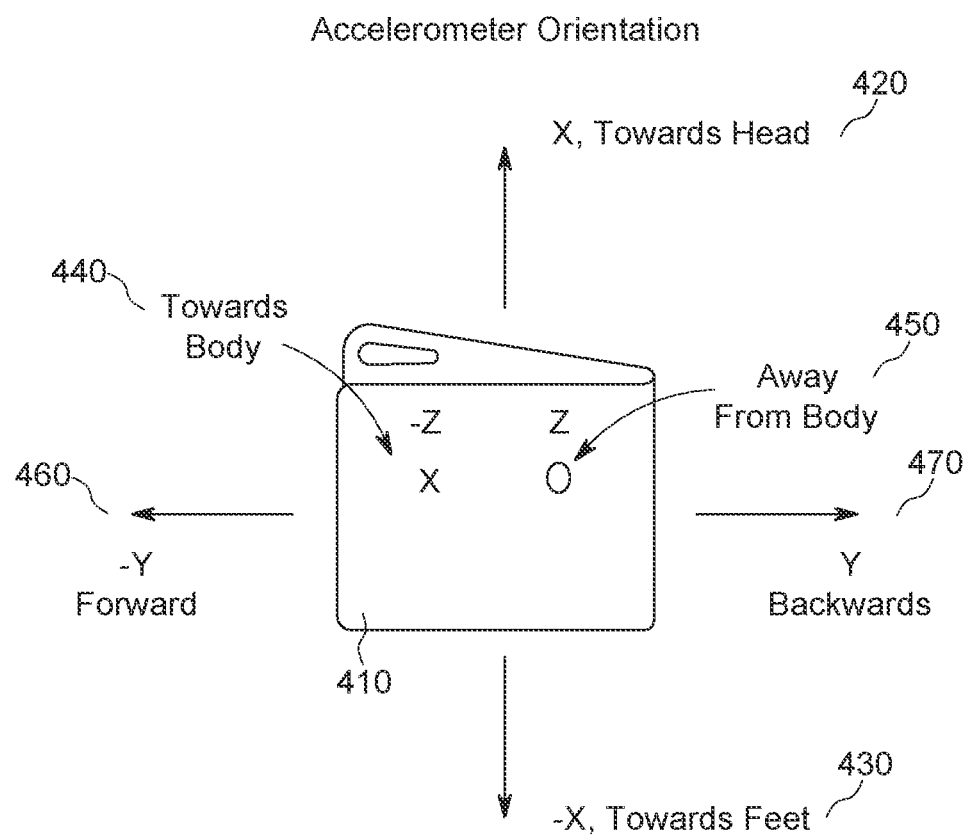
FIG. 4 is a schematic diagram of an orientation of an accelerometer.

FIG. 4 shows an exemplary implementation of accelerometer's orientation. Accelerometer 410 may be disposed inside a sensor enclosure, and the sensor enclosure may be attached to a subject during a plurality test for diagnosing cognitive conditions. In one implementation, accelerometer's x direction 420 point towards a subject's head or foot. Accelerometer's −z direction 440 may point towards or away from the subject's body. Accelerometer's −y direction 460 may point forward or rearward relative to the subject's orientation.

Figure 5:
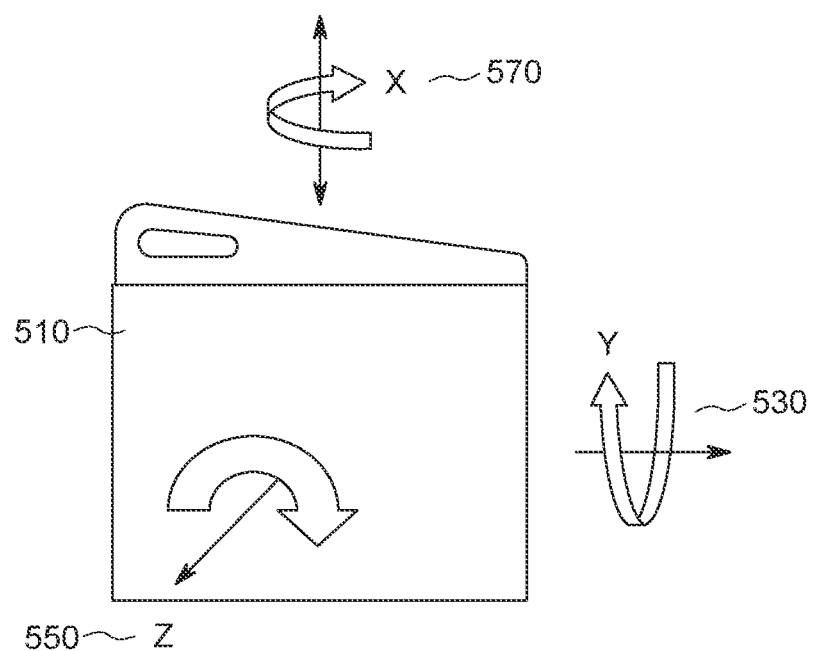
FIG. 5 is a schematic diagram of an orientation of a gyroscope.

FIG. 5 shows an exemplary implementation of gyroscope's orientation. Gyroscope 510 may be disposed inside a sensor enclosure, and the sensor enclosure may be attached to a subject during one or more tests for diagnosing cognitive conditions. The gyroscope may provide angular velocity of the sensor about each of three perpendicular axes. In one implementation, the gyroscope may provide an angular velocity about first axis 530 (e.g., aligned with y direction), an angular velocity about second axis 550 (e.g., aligned with the z direction), and an angular velocity about third axis 570 (e.g., aligned with the x direction).

The system may be capable of synchronizing video obtained by at least one video camera with the kinematic data from the sensors. The video may provide visually captured movement in conjunction with the kinematic data. For example, a marker may be displayed on the kinematic data that corresponds to a concurrently displayed video frame.

In one embodiment, during the diagnosis, one or more cognitive stimulus tests may be used alone or in conjunction with the composite signatures discussed above. The cognitive tests may include means of visual, audio, and/or tactile features.

The disclosure describes embodiments performing one or more tests to diagnose cognitive conditions. The one or more tests may be simple and the protocol written so it does not take medically trained personnel to administer. Data may be collected during the one or more tests without prejudice or examiner bias. The collected data may be processed for immediate review and/or recommendation. The collected or processed data/results may be sent to a medical expert by telemedicine for an opinion. In one implementation, the described methods may be performed on one or more members of a sports team prior to a game, so that a bench-mark profile may be established. After the game (or after a plurality of games, or during a game), the described methods may be performed on the same members of the sports team to diagnose cognitive conditions based on the corresponding bench-mark profile.

The present disclosure may have a high reproducibility due to the uniformity of the one or more tests. The present disclosure may include software to collect data of a subject, analyze data, and make comparisons of the data to one or more of the following: the subject's prior test data; normals in the subject's demographic; or specific abnormals.

In one embodiment, a mobile device as an off-the-shelf and commercially available technology may be used. For example, but not limited to, A smart watch or smart phone may provide a mobile means of providing one or more sensors to detect motion of a subject. The testing may be immediate, easy to administer, accurate, reliable, sensitive, specific, and inexpensive.

In another embodiment, a proprietary system may include MEMS to generate kinematic data. The MEMS sensors may transmit the kinematic data to a smartphone, a tablet, a desktop, a laptop, any computer device, or any cloud service for viewing, processing, and storage. The diagnosis process and results may be stored on a device or an on-line storage service, providing a permanent documentation.

In embodiments, there are three tests. A 2-point Discrimination test accompanies upper and lower extremity testing methods. The time to respond, initiate, and complete a test is recorded for comparison to prior tests and or established norms.

A MEMS device records the inherent motions, the motion traveled through space, the path, the speed, and the acceleration which will each form a "signature" to be compared to former testing and or the established norm by demographic data; age, gender, activity, prior testing, etc. The data collected is subject to correlation with the above information.

As one example, the tests can be performed on a team's players before the start of a sports season to establish individual and group norms, and then later for diagnostic purposes.

Glossary

Proprioception refers to the sense of self-movement, force, and body position. See Proprioception, Wikipedia, the free encyclopedia, last edited on 2 Jan. 2023, herein incorporated by reference.

Tactile perception and tactile perception testing, e.g., tactile edge orientation processing (TEOP) and testing, refer to the ability to test the perception of objects or judge sensations through the sense of touch. The term refers to judgments of spatial stimulation of the skin, patterns imposed on the skin, or sensory events involving stimulation of the skin (e.g., size and shape of objects, distinguishing objects, etc.) and the testing thereof.

A two-point discrimination test is a tactile perception test that tests the ability to discern that two nearby objects touching the skin are truly two distinct points not one. It is often tested with two sharp points during a neurological examination and in that context is used to reflect how finely innervated an area of skin is. See Two-point discrimination, Wikipedia, the free encyclopedia, last edited on 1 Nov. 2022, herein incorporated by reference.

Cognitive disorders are a type of mental health disorder that primarily affect cognitive abilities including learning, memory, perception, and problem solving. Cognitive disorders include dementia, Alzheimer's, brain trauma, or concussion. Examples of neurodevelopment disorders particularly in, but not limited to, children include attention-deficit/hyperactivity disorder (ADHD), autism, learning disabilities, intellectual disability (also known as mental retardation), conduct disorders, cerebral palsy, and impairments in vision and hearing. Cognitive disorders can also include frontotemporal degeneration, Huntington's disease, dementia with Lewy bodies, traumatic brain injury (TBI), Parkinson's disease, prion disease, and dementia/neurocognitive issues due to HIV infection. See Cognitive disorder, Wikipedia, the free encyclopedia, last edited on 2 Feb. 2023, herein incorporated by reference.

EXAMPLES

Example 1-Preliminary Question Test

A preliminary question test may be used for diagnosing cognitive conditions of a subject. The preliminary question test may be performed in an isolated and quiet location for the subject.

In one implementation, the subject may include an athlete, a warrior, a normal subject, or a suspected subject with at least one of a variety of cognitive clinical conditions, for example but not limited to, dementia, Alzheimer's, brain trauma, and concussion.

In one implementation, the subject may be in a sitting position. For example, the subject may sit upright and relaxed in a chair. In one implementation, the subject may be shown questions and be asked to provide response to each question. In one implementation, the subject may read each question and answer each question in a sequential manner.

In one implementation, general questions for the subject to answer may include at least one of: What is your full name? What is your first and last name? Where are you now? What month of the year is it? What day of the week is it? What city do you live in? What season is it?

In one implementation, the subject may provide a response at the end of each question. In one implementation, the order and questions may change slightly for each round of questioning.

In one implementation, a video camera records the subject and the subject's responses to questions. The video camera may record at 60 frames per second. In another implementation, the video camera may begin recording when the questions are shown to the subject either automatically or triggered by an operator.

In one implementation, the response may be graded by an operator or administrator at a certain scale. In one implementation, the certain scale may include a scale of from 1 to 4, for example, including 1, 2, 3, and 4.

In one implementation, the grading of the response may be determined based on the subject's ability to follow directions. In one implementation, a time duration of full response may be recorded by examining the video recording. In one implementation, the time duration may be documented. In one implementation, facial response of the subject may be examined and/or documented by an operator. The operator may examine the subject's facial response by observing the subject while the subject answers the questions or examining the video recording.

In one implementation, the facial response may include at least one of laughing, slur of speech, confusion, head position, or staring in space or other representative features.

In one implementation, there may be a time limit for the subject to provide a complete answer to each question, or there may be another time limit for the subject to provide answers to all tested questions. For example, there may be a time limit of 30 seconds for the subject to provide a complete answer to each question. For another example, there may be another time limit of 2 minutes for the subject to provide answers to all tested questions including five questions.

During the preliminary question test, data may be recorded in a variety of forms, including a paper format, a video format, an audio format, a text digital format, a binary digital format, and other digital storage formats. The data may also be recorded by a comprehensive form including one or more formats.

Example 2: What Time is it Test

In one embodiment, a "what time is it" (WTII) test may be used for diagnosing a subject's cognitive conditions. The WTII test may be based upon a common function of asking a subject "what time is it." In one implementation, the subject may include an athlete, a warrior, a normal subject, or a suspected subject with at least one of a variety of cognitive clinical conditions, for example but not limited to, dementia, Alzheimer's, brain trauma, and concussion.

In one implementation, a subject may wear a digital watch and a device including at least one MEMS sensor on a dominant upper extremity on the dorsum of the distal forearm, near the wrist of the subject.

Figure 6:
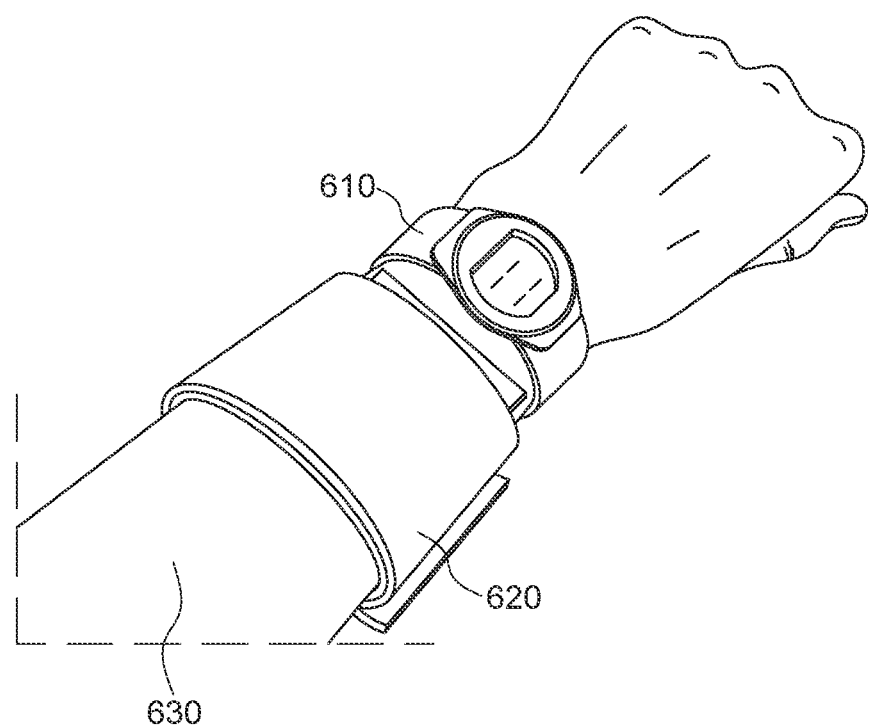
FIG. 6 is a schematic diagram of a location of the system during "what time

Referring to FIG. 6, digital watch 610 may be disposed on a subject's arm 630. The digital watch may display a time in digital numbers corresponding to hours, minutes, and seconds. Device 620 includes at least one MEMS sensor that may be disposed adjacent to digital watch 610.

In another implementation, a subject may wear a watch with second, minute, and hour hands. The watch may be a digital one or a traditional mechanical watch. The subject may read a time by reading positions of the second, minutes, and hour hands.

In one implementation, the device include a MEMS accelerometer and a gyroscope sensor.

In one implementation, the subject may sit upright and relaxed in a chair. The subject may have dominant arm hanging straight by their side, which may provide a clear starting position which may be easily detectable in accelerometer data.

In one implementation, the subject may be instructed to start to move an arm of the subject to tell time when an operator states "go", and then may be instructed to return the arm to a side of the subject hanging straight down upon completion.

In one implementation, the subject may be asked to provide the response in hours and minutes when the subject answers the question.

In one implementation, the subject may be asked not to provide the response in seconds.

In one implementation, a system may begin collecting data upon the word "it" when the operator provides the question of "what time is it", which may be recorded as the start of the motion time.

In one implementation, the system may stop collecting data from the at least one MEMS sensor upon the completion of subject's response. The completion of the subject's response may be the time when the arm of the subject hangs straight down by the side the subject. In another implementation, the completion of the subject's response may be determined by the operator.

In one implementation, the response of the subject may be graded based on at least one of the following: 1 point awarded for correct time; differences in arm motion being evaluated for each round; or ability of the subject to follow directions.

Here, the "correct time" may refer to a time range around the time displayed on the watch used by the subject, for example, ±1 minutes of the time displayed on the watch used by the subject.

In one implementation, a stopwatch may be used to measure the time from the start to the completion of the WTII test. In one implementation, there may be a time limit for the subject to complete the WTII test. For example, there may be a time limit of 30 seconds for the subject to complete the test.

The present disclosure describes another embodiment of a method for performing a WTII test. Optionally, the method may include turning on a computer for recording and verifying the computer. Optionally, the method may include getting ready with a stopwatch and verifying operation of the stopwatch or other time measuring device. Optionally, the method may include identifying uninjured dominant upper extremity of a subject.

Optionally, the method may include advising the subject about what the subject is going to do. Optionally, the method may include applying the timer/watch to dorsum of the subject's wrist. Optionally, the method may include giving instructions of the exam or test.

In one implementation, an operator may not use the word "test". In another implementation, the instructions may include: "you have a time piece or wrist watch on your dominant hand side, start by resting your hand on the corresponding thigh, and sit quiet for a moment and I will tell you what to do."

Optionally, the method may include determining whether the subject follows the instructions. Optionally, the method may include recording yes or no as a result of the determination whether the subject follows the instructions. Optionally, the method may include recording an explanation in response to the determination that the subject does not follow the instructions. Optionally, the method may include asking the subject to repeat the test for at least one time.

Optionally, the method may include recording the number of times that it is necessary for the subject to repeat to determine that the subject follows the instructions. Optionally, the method may include recording whether the subject is unable to follow the instructions or whether the subject is unwilling to follow the instructions.

Optionally, the instructions may further include "now we are ready; and I am going to ask you what time it is. Do not start until I give the word to start. I will repeat what I just said and then you will start, but wait for me to say, 'What time is it on the watch?'"

Optionally, the method may include recording the time of day with either am or pm by an operator. Optionally, the method may include recording the time in data sheet. Optionally, the method may include creating one or more drop down boxes for entering time. Optionally, the method may include starting a timer on a START command to record the starting time point. Optionally, the method may include instructions which includes "START: Please tell me what time it is on the watch and return you hand to your side."

Optionally, the method may include recording the time of day expressed by the subject with either am or pm and entering the time in data sheet by either the subject or the operator. Optionally, the method may include determining whether the test is successful. In response to the determination that the test is successful, the method may include turning off a recording device, for example a computer device.

Optionally, the method may include replaying a video recording for confirmation. Optionally, the method may include complimenting the subject with words of encouragement, for example but not limited to, "You are doing fine."

The WTII test may measure any one or more of a time duration, time sequence, and body part's motion when the subject responds to the instructions or questions of the WTII test. The test may include and combine many diagnostic features providing a simple and inexpensive test that may be administered anywhere by anyone of any level of training.

Results of the test may be documented and stored to provide a permanent record for immediate or future review. In one implementation, the results may have the ability to compare to prior reports for the same or different subject. In another implementation, the results may be compared to a normal cohort of a same demographic as the subject or may be compared to known pathological state of any condition or disease.

In another implementation, the documentation or the video recordation of a subject's motion provides a means to monitor progress of the subject in response to therapy, treatment, or rehabilitation. For example, in sport concussion based on protocols, the results may be used to determine whether or when the subject is allowed to return to competition in sports.

Figure 7:
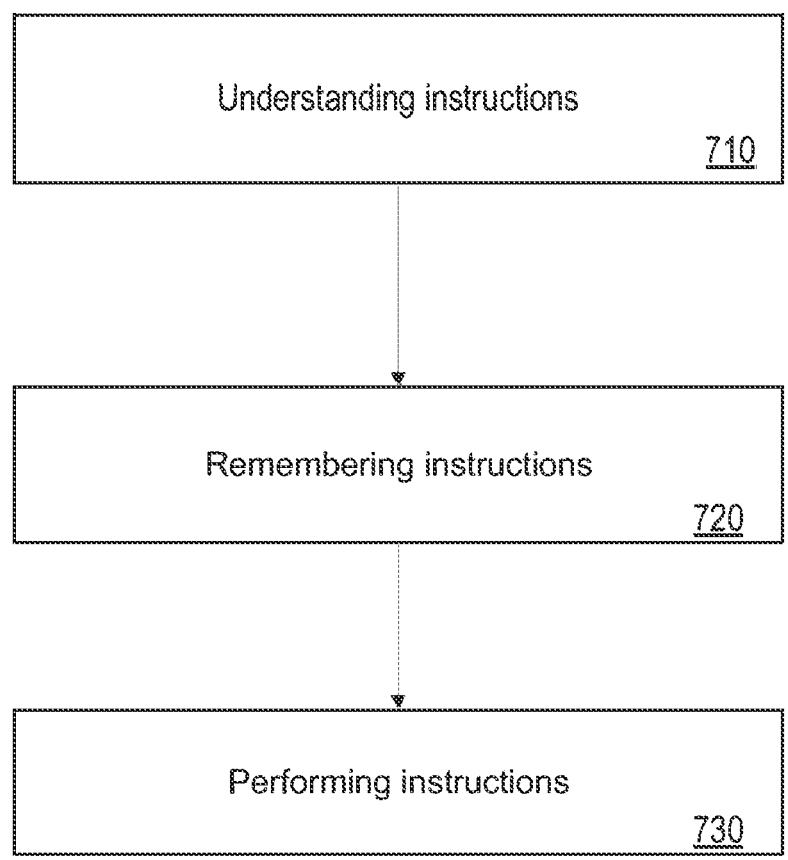
FIG. 7 is a flow diagram of an embodiment for performing a cognitive test for diagnosing cognitive conditions.

In another embodiment, test 700 for diagnosing cognitive condition may include the following general steps, as shown in FIG. 7.

Step 710 may include understanding instructions by a subject. The instructions may be a set of instructions, or a single instruction. A set of instructions may be provided to a subject, so that the subject may understand the set of instructions. The set of instructions may be verbal or written instructions. In one implementation, the verbal instructions may be provided by another person or played as pre-recorded audio. The verbal instructions may be provided to the subject for one or more times within a certain amount of time duration. In another implementation, the written instructions may be provided on a piece of paper or shown on a display, such as a computer monitor or a projector screen. The written instructions may be provided to the subject within a certain limited duration.

In the embodiment of using WTII test, the instruction is "what time is it, which is not complicated and common to everyday life. In another implementation, the instruction may further include the movement of the upper extremity to tell the time and speak it out loud, and/or followed by replacement of the upper extremity to the starting position.

Step 720 may include remembering the instructions by the subject. After understanding the instructions, the subject may need to remember the instructions. In one implementation, the subject may also need to remember the order of the instructions.

In the embodiment of using "what time is it" test, the instruction may be easy to remember as one common to daily routine. The instruction may require no prior training or special instruction to fulfill. In one implementation, the instruction may be potentially challenging as there are several successive components. The instruction may have multiple physical motions to position the watch for reading. The instruction may need visualization of the watch with acuity of visualization. The instruction may need to read the time on the watch. The instruction may also need comprehension of time. The instruction may need verbal skill to report the time. The instruction may need the subject to return the upper extremity to the starting position at the end of task.

Step 730 may include performing the instructions by the subject. The set of instructions may instruct the subject to perform a task. While remembering the instructions, the subject may perform the task by performing the instructions. A goal for the subject performing the instructions is to perform the test with dispatch and accurately.

During performing the instructions, motion signatures, audio record, and/or video record may expose some variations for the subject in comparison with a group of normal subjects. The variations may include at least one of: a delay, a speed, 3D motion in space, a range of motions, an interruption in movements, tremors, convulsions, and/or a spasticity.

[Based on the performance of the subject, the method of the present disclosure may: provide composite signatures for an age, a gender, and demographics; produce composite signatures as representative of various pathological conditions; produce a narrative and graphic procedure to diagnose cognitive conditions, including but not limited to, concussion, Alzheimer's, dementia, low IQ, and the like; provide a means to recommend medication; provides a means to project the prognosis; provide a means to recommend rehabilitation measures; provide a means to recommend living arrangement; provide a means to recommend nursing care; or provide a part of a head injury sport protocol to determine whether or when the subject may be allowed to return to work or return to sports.

A system for WTII test may include a monitoring device on a subject's extremity for transmitting motion data to a recording device. The recording device may be a computer, a smart phone, a tablet, or the like. In one implementation, one or more MEMS may be placed on a dorsal side of a subject's wrist. The subject may have a hand placed in a lap, over an abdomen, or just above a pubis. A device may be placed nearby to receive and record data transmitted from the one or more MEMS sensors. In one implementation, the devices may be off-shelf and commercially available technologies/devices, for example, one or more MEMS may be a smartwatch or a smartphone.

Optionally, the subject under WTII test may be video recorded throughout or a portion of the WTII test.

An extremity under WTII test may be a dominant side. In one implementation, however, when it is questioned if one side has numbness to the exclusion of the other side, the numb side may be under WTII test. In another implementation, at the discretion of an operator/examiner, both sides may be under WTII test. The operator/examiner may be a person supervising the WTII test.

In one implementation, prior to being given the instructions, the subject sits upright. In another implementation, prior to being given the instructions, the subject may be in a supine resting position. A recording device with visible time displayed is placed on a dorsal side of a subject's wrist. The subject may have a hand placed in a corresponding mid-thigh.

When an instruction, "what time is it?" is provided to a subject, the subject may understand the instruction or may not understand the instruction. When the subject understands the instruction, the subject may without delay raise a forearm with rotation to see a face of a wristwatch attached on a dorsum of the wrist, may verbally state the time seen on the wrist watch, and then may return the forearm to a resting position. The resting position may not necessarily be an index position on the abdomen. In one implementation, a start signal may be provided to the subject, so the subject may begin performing the instruction after receiving the start signal. In another implementation, there may be no start signal provided to the subject, so the subject may take the instruction as the start signal and begin performing the instruction after receiving the instruction.

When the subject performs the instruction, the device may, according to the data transmitted from the MEMS sensors, obtain one or more of the following: ability to hear the instruction; ability to understand the instruction and follow the instruction; ability to begin performing the instruction; ability to finish performing the instruction and speak the time correctly; any stoppage and a step where a stoppage occurs; maximum rotation and elevation compared to normal group; a first time interval between a first time point when the start signal is provided and a second time point when the subject raises the forearm; a second time interval between the first time point when the start signal is provided and a third time point when the subject verbally states the time displayed on the watch; a third time interval between the third time point when the subject verbally states the time displayed on the watch and a fourth time point when the subject returns the forearm to the resting position; ranges of the motions of the at least one body part of the subject; an acceleration of the motions of the at least one body part of the subject; a rotation of the motions of the at least one body part of the subject; a speed of the motions of the at least one body part of the subject; an angulation of the motions of the at least one body part of the subject; a composite tacking of the watch in space; recording of any demeanor at completion of performing the instruction; graphic signature of the subject; an accuracy of a verbally stated time relative to the time displayed on the watch; a return accuracy related to a return placement of the forearm; or an all over assessment of control of the body part as compared to normal and other pathological conditions.

When the subject performs the instruction, the device may, according to the data transmitted from the MEMS sensors, record one or more of the following: time lapse after commend to start movement; time lapse to respond verbally to the time of the day; any delay in respond by movement measurement; time to return or lower the upper extremity; excursion of the motion as to range of motion; acceleration of the movement; rotation of the movement; speed of the movement; angulation of the movement; composite tracking of the wrist monitoring in space; accuracy of the response to time of day displayed on the wrist device; or return placement of the upper extremity.

Figure 8A:
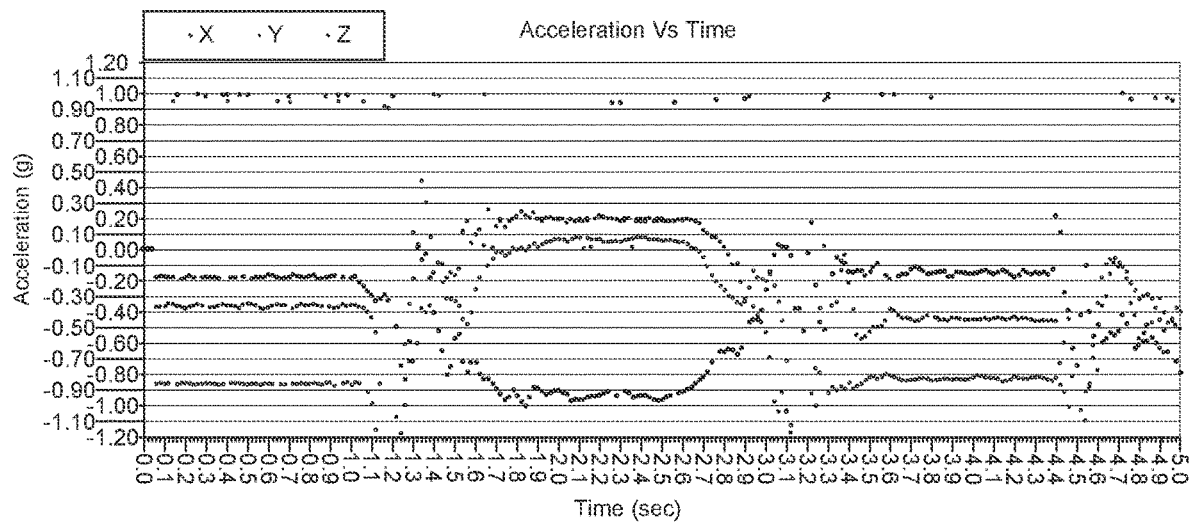
FIGS. 8A and 8B show a set of exemplary data collected by the system during "what time is it" test.

Referring to FIG. 8A, a 3-dimensional acceleration data along x, y, and z axes may be obtained from an accelerometer MEMS sensor, which may be shown as a function of time in seconds.

Figure 8B:
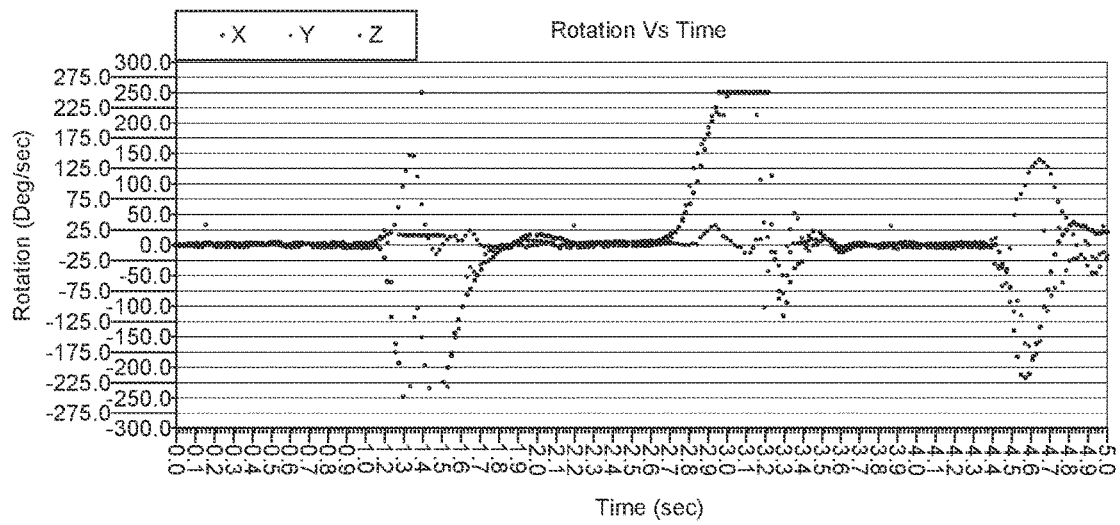

Referring to FIG. 8B, a 3-dimensional rotation data around x, y, and z axes may be obtained from a gyroscope MEMS sensor, which may be shown as a function of time in seconds.

Optional scoring may be kept in a simple format for the clinical application. The scoring may be first measured on an estimated extent of completion in the time allotted. The recording, data or video, may be used to confirm the extent or for further study. The scoring may include assigning 4 points when the subject completes the test in a certain time limit; assigning 3 points when the subject completes % of the test in the certain time limit; assigning 2 points when the subject completes ½ of the test in the certain time limit; assigning 1 point when the subject completes % of the test in the certain time limit; and assigning 0 point when the subject fails to start the test in the certain time limit.

In one embodiment, based on the cognitive test, pathological variations may be obtained as one or more of the following: lack of understanding; delay in initiation of movement; incomplete positioning to read the time of day; unable to read the time on the watch; erroneous relating the time to the day; or extraneous return or not to a resting position.

A summary form may be generated by computer and attached to an end of the documented report data. In one implementation, the summary form may include examiner's observations, observer's additional comments, and/or recommendations from one of examiner or observer.

During a WTII test, data may be recorded in a variety of forms, including a paper format, a video format, an audio format, a text digital format, a binary digital format, and other digital storage formats. The data may also be recorded by a comprehensive form including one or more formats.

Example 3: Tactile Edge Orientation Processing Test (TEOP)

Under a TEOP test, a subject may be instructed to reach into a bag, a purse, or a pocket containing one or more objects and remove a designated object. The TEOP test is based on tactile edge orientation processing, or the mnemonic TEOP. During TEOP test, time durations, time sequences, and/or motion of the subject in response to the instructions may be measured and recorded. In one implementation, the objects may include coins and/or a key. The coins may include at least one of a penny, a nickel, a dime, a quarter, or a foreign coin with a different shape. The key may include one or more metal door key.

Optionally, the subject under TEOP test may be video recorded during a whole process or a portion of the TEOP test.

TEOP tests may require the subject to understand the instructions and may test a palpation, a sensibility, a recognition, a cognition, a proprioception, a neuromuscular coordination, and/or a verbal response of the subject in response to the instructions.

In one implementation, prior to being given the instructions, a subject may be in a sitting position. A recording device may be placed on a dorsal side of a subject's wrist. Depending on specific circumstances, the subject may have a hand placed in a standard position, on a table top, or in a corresponding mid-thigh.

In one implementation, the subject may wear a device including at least one MEMS sensor. The at least one MEMS sensor may include at least one of MEMS accelerometer or gyroscope. The at least one MEMS sensor may be disposed on dominate arm of the subject, near the wrist.

In one implementation, the subject may be given a black bag containing a plurality of objects. For example, but not limited to, the black bag may contain four objects including three different sizes of coins and a key.

In one implementation, the subject may sit upright and relaxed in a chair with dominant arm hanging straight by a side of the subject. The subject may hold the black bag in a non-dominant hand.

In one implementation, the subject may be instructed to start arm movement to select a specified named object from the black bag. For example, the specified named object may be a coin of intermediate size, e.g., a nickel or quarter.

In one implementation, the subject may start arm movement to select the specified named object when a "GO" instruction is given by an operator, and after selecting the specified named object, the subject may raise object to an eye level of the subject for confirmation.

In one implementation, the selected object may be returned to the black bag before selecting next object. In one implementation, the subject may read an order of object selection from a computer screen. The order of the object selection may change from one round to next round.

In one implementation, the MEMS sensor may begin collecting data at the time point when the "GO" signal is given. The subject's starting time point may be recorded, considering a reaction time.

In one implementation, the MEMS sensor may stop collecting data at a time point when all objects are selected by the subject.

In one implementation, the subject's raising the arm may be measured by the MEMS sensor and recorded, thus the sensor data may determine exact time points when the objects are selected.

In one implementation, an operator or an administrator may determine whether a correct object is selected based on an order displayed on a display.

In one implementation, response of the subject may be graded following at least one of the following methods: 1 point is awarded for selecting correct object; differences in arm motion may be evaluated for each round; time from start to object at eye level may be recorded for selecting each object in each round; or ability of the subject to follow directions/instructions may be evaluated.

In one implementation, there may be a time limit for the subject to complete selecting one object, and/or there may be another time limit for the subject to complete a test of selecting one or more objects. For example, there may be a time limit of 10 seconds for the subject to selecting one object. For another example, there may be another time limit of 30 seconds to complete the test of selecting four objects.

The present disclosure describes another embodiment of a method for performing a TEOP test.

Optionally, the method may include a time limit for a subject to respond. For example, the time limit may be 30 seconds, so that the subject may stop after 30 seconds and an operator may determine how far the subject has completed the assigned task within the time limit.

Optionally, the method may include one or more instruments. The instrument may include a stopwatch, a bag, and a plurality of other objects. Optionally, the bag may be a black bag or any other non-transparent bag. Optionally, the plurality of objects may include coins and a key. For example, the coins may include various sized coins, e.g., a penny, a dime, and a quarter.

Optionally, the method may include instructions. The instructions may include the following instructions: Advise that there are several objects in the bag; You will be asked to reach into the bag and remove the object that I requested; The bag will be placed in your non-dominant hand; Open the bag and reach in with your dominant hand and remove the [state one of these; penny, dime, nickel, quarter or key] and show it to me; Then put the object back in the bag and close the bag.

Optionally, the method may include asking the subject whether the subject understands the instructions and recording yes or no for the subject's answer. Optionally, the method may include, when the subject does not understand the instructions, recording a problem or an issue associated with the subject.

Optionally, the method may include, when the subject does not understand the instructions, repeating the instructions for one or more times, and recording a number of times of repeating the instructions. Optionally, the method may include an instruction to the subject, the instruction may include "do not start until I give the command." Optionally, the method may include verifying a functionality of a stopwatch. Optionally, the method may include giving a "Go" command to the subject and starting the stopwatch at the same time. Optionally, the method may include stopping testing after a certain time limit. For example, but not limited to, the certain time limit may include 30 seconds. The subject may stop continuing the test when the certain time limit is reached.

Optionally, the method may include recording an extent of success based on at least one of the following: whether the subject has started the test; whether a hand of the subject is in the bag; whether the hand of the subject is out of the bag; whether the subject completes the test successfully.

Optionally, the method may include identifying and recording the objects selected by the subject from the bag. Optionally, the method may include evaluating whether the object selected by the subject are correct and recording correctness of the selected object. Optionally, the method may include repeating the test with a set of different objects. Optionally, the method may include providing words of encouragement to the subject. The words of encouragement may include "you are doing fine."

When an instruction of a TEOP test is provided to a subject, the subject may understand the instruction or may not understand the instruction. In another implementation, further instructions or expectation may be provided to the subject: move the upper extremity to place a hand into a bag containing objects; reach in the bag; pull out a designated object and display it to an examiner; and/or return the upper extremity to a starting position. The objects may include coins and a key, and the designated object may be the key.

When the subject understands the instruction, the subject may without delay initiate and complete the instruction. When the subject performs the instruction, the recording device may record one or more of the following: time lapse after commend to start movement; time lapse to complete the test; any delay in respond by movement measurement; excursion of the motion as to range of motion; acceleration of the movement; rotation of the movement; speed of the movement; angulation of the movement; composite tracking of the wrist monitoring in space; accuracy of the picking the designated object; or return placement of the upper extremity.

Figure 9A:
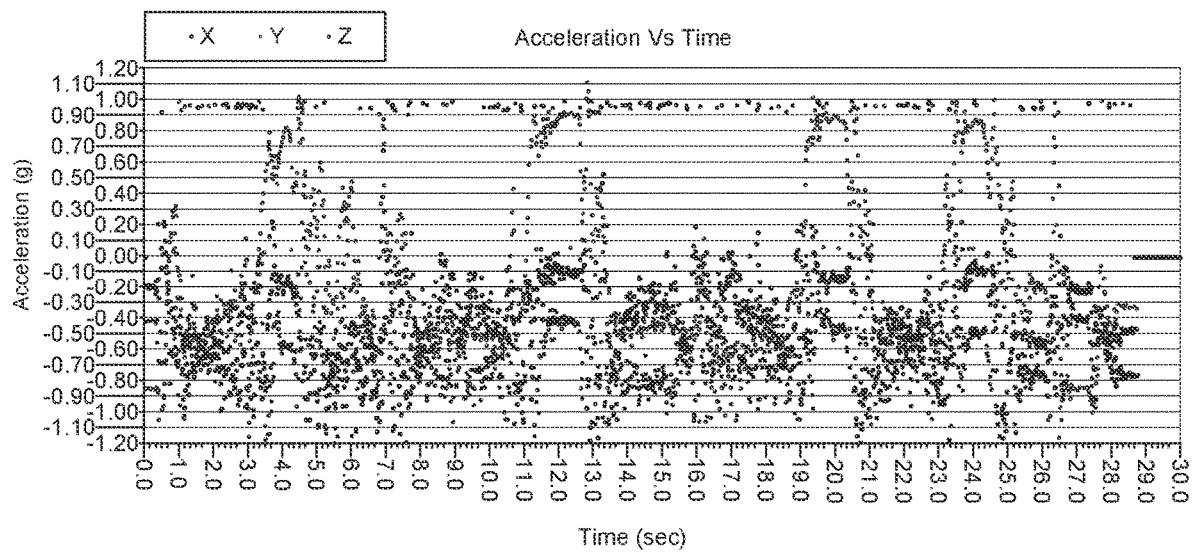
FIGS. 9A and 9B show a set of exemplary data collected by the system during "tactile edge orientation processing" test.

Referring to FIG. 9A, a 3-dimensional acceleration data along x, y, and z axes may be obtained from an accelerometer MEMS sensor, which may be shown as a function of time in seconds.

Figure 9B:
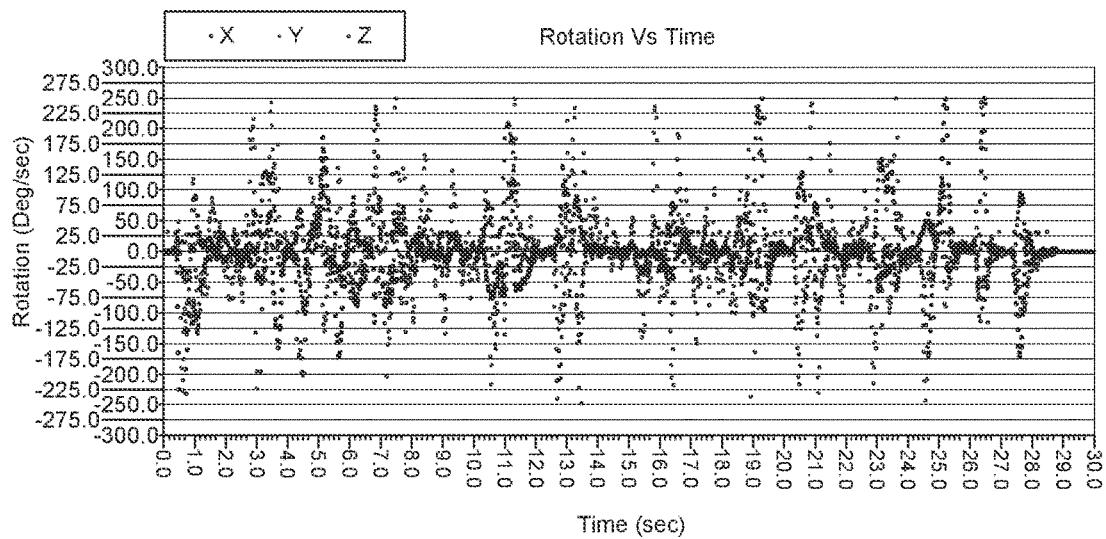

Referring to FIG. 9B, a 3-dimensional rotation data around x, y, and z axes may be obtained from a gyroscope MEMS sensor, which may be shown as a function of time in seconds.

The scoring may be kept in a simple format for the clinical application. The scoring may be first measured on an estimated extent of completion in the time allotted. The recording, data or video, may be used to confirm the extent or for further study. The scoring may include assigning 4 points when the subject completes the test in a certain time limit; assigning 3 points when the subject completes ¾ of the test in the certain time limit; assigning 2 points when the subject completes ½ of the test in the certain time limit; assigning 1 point when the subject completes ¼ of the test in the certain time limit; and assigning 0 point when the subject fails to start the test in the certain time limit.

In one embodiment, based on the cognitive test, pathological variations may be obtained as one or more of the following: lack of understanding; delay in initiation of movement; incomplete positioning into the bag; erroneous picking of the designated object; or extraneous return or not to a resting position.

A summary form may be generated by computer and attached to an end of the documented report data. In one implementation, the summary form may include examiner's observations, observer's additional comments, and/or recommendations from one of examiner or observer.

During a TEOP test, data may be recorded in a variety of forms, including a paper format, a video format, an audio format, a text digital format, a binary digital format, and other digital storage formats. The data may also be recorded by a comprehensive form including one or more formats.

Example 4: Lower Extremity Leg Movement Test

A lower extremity leg movement (LELM) test is commonly used for diagnosing cognitive conditions of a subject. The LELM test may test for a lower extremity of the subject in the present disclosure including the MEMS measurements. [00159] A lower extremity under LELM test may be an effected side or a dominant side. In one implementation, however, when it is questioned if one side has numbness to the exclusion of the other side, the numb side may be under LELM test. In another implementation, at the discretion of the examiner supervising LELM test, both sides may be under LELM test.

During LELM test, a subject may sit upright or in a supine resting position. A recording device including one or more MEMS sensor may be placed on a selected lower extremity side just above an ankle with the recording device on the surface of the tibia. A data recording device may receive data transmitted from the recording device.

Figure 10A:
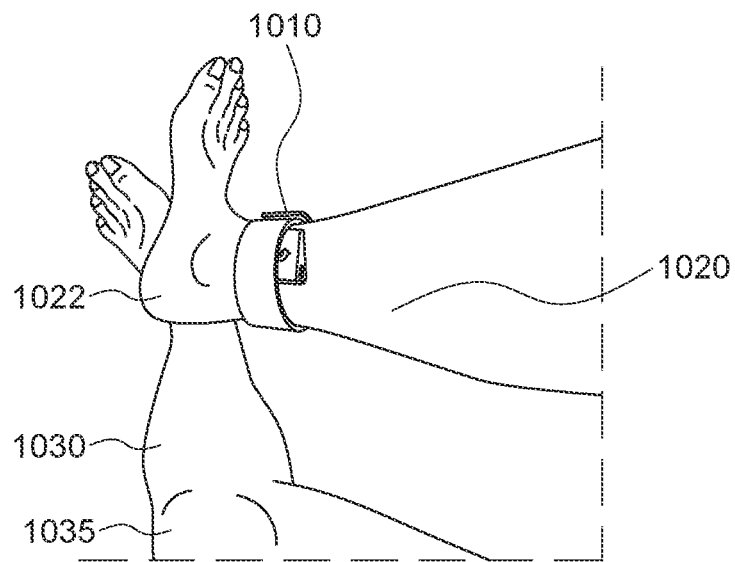
FIGS. 10A, 10B, and 10C are schematic diagrams of a location of the system during "lower extremity leg movement" test.

Referring to FIG. 10A, in one implementation, device 1010 may be disposed on a right lower extremity 1020 above an ankle. Heel 1022 of the right lower extremity 1020 may be placed on an inner aspect of an ankle of the opposite leg 1030.

Figure 10B:
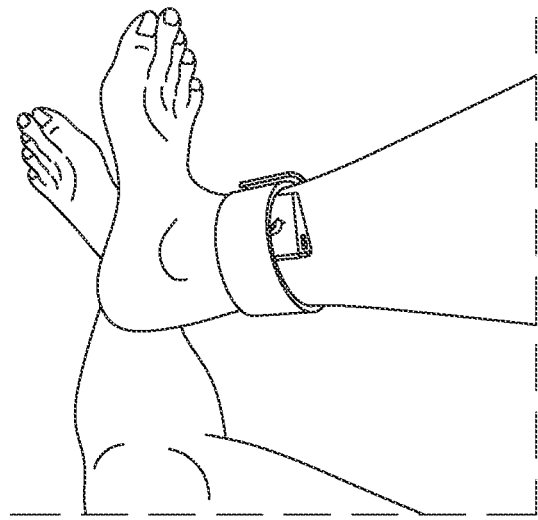
Figure 10C:
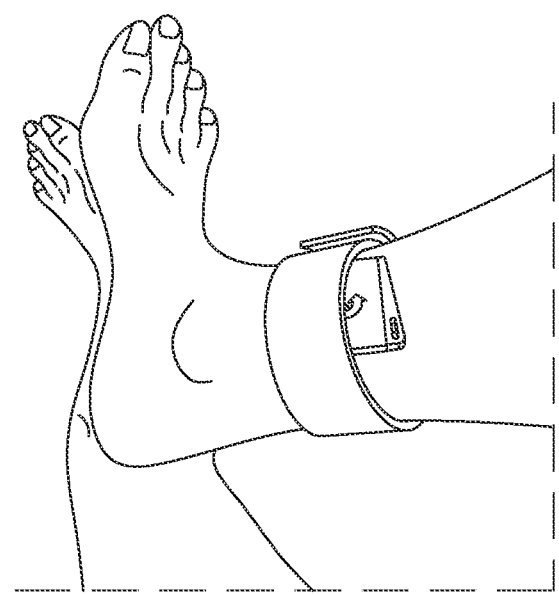

Referring to FIG. 10B and FIG. 10C, the subject may slide the heel 1022 up the opposite tibia to knee 1035 of opposite leg 1030. The subject may then return heel 1022 to the starting place on the ankle and stop. After a momentary pause, the subject may return the test lower extremity to the original position, for example, flat on the floor.

In one embodiment, a subject may be advised about the procedure of the test, the nature of the recording device and its purpose to record the motion of the lower extremity. Optionally, the examiner may demonstrate how the test is performed. For the more demented subject, the subject may be shown how this is done with a preliminary instructions and passive movement of the test extremity by the examiner.

It may be presumed that a normal subject may understand the instructions and may begin moving as instructed without delay. The test may be completed when the subject returns the lower extremity to the starting position. The conclusion of the test in some may be when the quit at a point short of the starting position.

In one implementation, the subject may wear a device including at least one MEMS sensor just above an ankle of a dominant leg of the subject. For example, the subject may wear a device containing at least one of MEMS accelerometer and gyroscope. The device may be disposed just above the ankle and facing outwards of a dominant leg of the subject.

In one implementation, the subject may sit upright and be relaxed in a chair with both feet on the floor. In one implementation, the subject may be without shoes.

In one implementation, the subject may be instructed to place a heel of a foot of a dominate leg on opposite leg's shin bone next to an ankle area of the opposite leg and slide the heel up a front around shin bone of the opposite leg to a knee of the opposite leg and then slide back down the shin bone of the opposite leg to the ankle area of the opposite leg and then place the foot flat on floor.

In one implementation, the subject may, after the instructions and when an operator/administrator states "Go", begin motion. In one implementation, the MEMS sensor may begin collecting data at the time point when the operator states "Go", and thus the subject's starting time point of motion may be recorded. Optionally, a reaction time of the subject may be considered. In one implementation, the MEMS sensor may stop collecting data when subject's foot of dominate leg is back flat on the floor.

In one implementation, response of the subject may be graded based on at least one of the following: an evaluation of differences in leg motion for each round; a time duration from start to stop for each round; and ability of the subject to follow directions.

In one implementation, there may be a time limit for the subject to complete the test. For example, there may be a time limit of 30 seconds for the subject to complete the test.

The present disclosure describes another embodiment of a method for performing a lower extremity leg movement test.

Optionally, the method may include instructions to a subject. The instructions may include one or more of the following: We are going to test your coordination of your lower extremity; You will either be sitting or lying down on the table; You will remove your shoes and socks and roll up or remove pants to expose the leg up to and above the knee; I will place a sensor on your leg, just above the ankle; I will ask you to place your right heel on the left leg shin bone just above the ankle; I will demonstrate or place your leg to that sport; I will then ask you to run that heel up the shin bone to the knee and back again; I will demonstrate; or After that we will reverse the procedure; the left heel to run up your right shin bone to the knee.

Optionally, the method may include determining whether the subject understands the instructions. Optionally, the method may include, when it is determined that the subject understands the instructions, instructing to the subject with "get set but do not start until I give the 'Go' command." Optionally, the method may include confirming that the sensor and recording computer is operational.

Optionally, the method may include disposing a recording device on a right leg just above an ankle of the subject. Optionally, the method may include recording data from at least one MEMS sensor. Optionally, the method may include recording video data from a video camera. Optionally, the method may include placing a recording device on a left leg just above an ankle of the subject and repeating the instructions.

Optionally, the method may include recording data from at least one MEMS sensor and/or video camera when the subject performs the test with the left leg.

Optionally, the method may include recording documentation on a computer. Optionally, the method may include confirming the documentation on the computer. Optionally, the method may include providing words of encouragement to the subject. The words of encouragement may include "You did fine." Optionally, the method may include disposing the subject, for example, at home, at clinic, or at hospital.

Optionally, the method may include performing a short-memory check. The short-memory check may include asking the subject one or more questions, which may include at least one of the following: What time was it on the watch test? What was the first coin you found? Or Which side heel did you run up the opposite shin bone?

Optionally, the method may include determining whether an answer of the subject to the question during short-memory check is correct. Optionally, the method may include recording the answer and/or correctness of the answer.

Optionally, the method may include scoring the subject based on performance of the subject during the test.

The scoring may be kept in a simple format for the clinical application. The scoring may be first measured on an estimated extent of completion in the time allotted. The recording, data or video, may be used to confirm the extent or for further study. The scoring may include assigning 4 points when the subject completes the test in a certain time limit; assigning 3 points when the subject completes ¾ of the test in the certain time limit; assigning 2 points when the subject completes ½ of the test in the certain time limit; assigning 1 point when the subject completes ¼ of the test in the certain time limit; and assigning 0 point when the subject fails to start the test in the certain time limit.

The recording may go on for patient satisfaction and compliance and removal of frustration of failure, but the document is time sensitive.

Optionally, the method may include evaluating and recording one or more of the following: accuracy for completion of the test; tremors of the subject during the test; the path of movement compared to normal on the computer read out; or successful identification of the object by the subject.

When the subject performs the instruction, the recording device may record, as documented record, one or more of the following: time lapse after commend to start movement; any delay in the subject's response to the instructions; time to perform each phase of the tests; time to return to the starting position; excursion of the motion as to range of motion; acceleration of the movement; rotation of the movement; speed of the movement; angulation of the movement; composite tracking of the wrist monitoring in space as the "signature"; or return placement of the lower extremity.

Figure 11A:
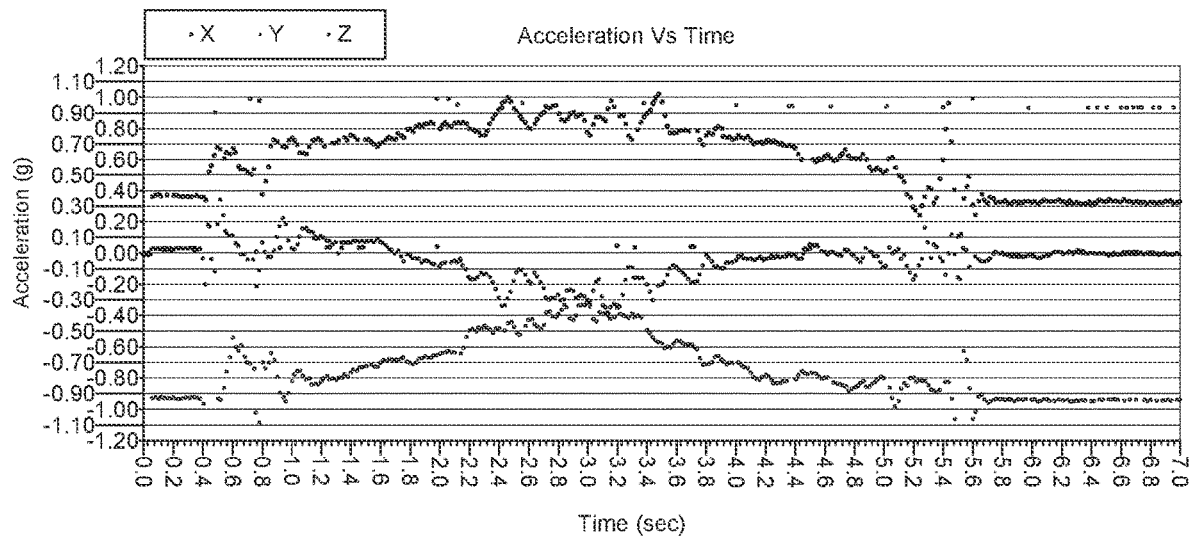
FIGS. 11A and 11B show a set of exemplary data collected by the system during "lower extremity leg movement" test.

Referring to FIG. 11A, a 3-dimensional acceleration data along x, y, and z axes may be obtained from an accelerometer MEMS sensor, which may be shown as a function of time in seconds.

Figure 11B:
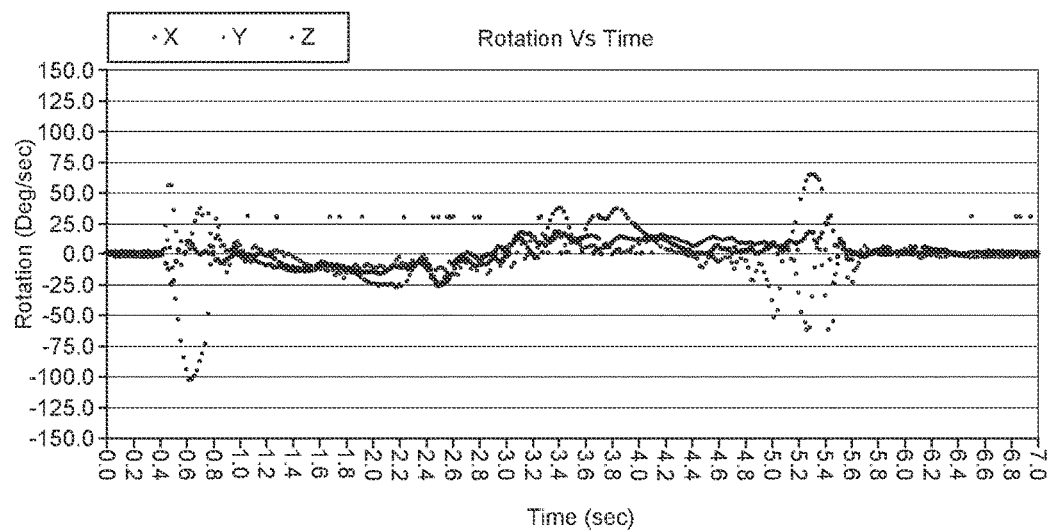

Referring to FIG. 11B, a 3-dimensional rotation data around x, y, and z axes may be obtained from a gyroscope MEMS sensor, which may be shown as a function of time in seconds.

In one embodiment, based on the cognitive test, pathological variations may be obtained as one or more of the following: lack of understanding; delay in initiation of movement; incomplete positioning; unable to follow instructions; or extraneous return or not to a starting position.

A summary form may be generated by computer and attached to an end of the documented report data. In one implementation, the summary form may include examiner's observations, observer's additional comments, and/or recommendations from one of examiner or observer.

During a LELM test, data may be recorded in a variety of forms, including a paper format, a video format, an audio format, a text digital format, a binary digital format, and other digital storage formats. The data may also be recorded by a comprehensive form including one or more formats.

Example 5: Tests for Other Cognitive Conditions

In another embodiment, when the cognitive conditions are related to a concussion, the method for diagnosing the cognitive conditions may include the following: Immediate diagnosis; Protocol; Treatment selection; Measurement of treatment benefit; Return to sport or job.

When the cognitive conditions are related to a brain trauma, the method for diagnosing the cognitive conditions may include the following: Extent of injury; Consequences of injury; Prognosis; Treatment recommendations.

When the cognitive conditions are related to a dementia, the method for diagnosing the cognitive conditions may include the following: Early recognition and prophylactic treatment; Specific diagnostic category; Treatment recommendations; Prognosis.

When the cognitive conditions are related to a Alzheimer's condition/disease, the method for diagnosing the cognitive conditions may include the following: Early recognition and prophylactic treatment; Confirm the clinical impression; Treatment recommendations; Prognosis; Extended for early diagnosis for family members.

Example 6: Concussion the one or more tests for diagnosing cognitive conditions may include different parameters and variations for an athlete who may have a concussion or a subject who may have dementia.

The sports arena and television may have drawn public awareness to the concussion. For example, the publicity concerning National Football league players with the consequences of head injuries with subsequent depression, dementia, and some notable suicides. The increased awareness may result in many different assessment modalities; sport concussion assessment tool (SCAT), vestibular/ocular-motor screening (VOMS), King-Devick test, and international brain bee (IBB). The SCAT may be a standardized tool for evaluating injured athletes for concussion and can be used in athletes aged from 13 years and older. The SCAT may be a screening evaluation tool designed for use only by qualified first responders or medical professionals. The SCAT score does not independently determine the diagnosis of a concussion, nor does it independently determine the injured athlete's recovery or return to play status. Such determination can only be made by a medical professional who has experience in the treatment of sport concussion. The King-Devick test may be based on measurement of the speed of rapid number naming, and then may capture impairment of eye movements, attention, language, and other correlates of suboptimal brain function. The IBB may include a neuroscience competition for a group of people, for example, teenagers.

Imaging testing methods like the MRI may have a limited role, perhaps to rule out brain hemorrhage. Present day information may indicate that evaluation of a concussion is functional more than structural. The existing clinical laboratory tests or practical biomarkers available may not be sufficient to assist in this matter.

Since concussions are variable and now recognized as highly individualized, all existing functional tests may have weaknesses. The weakness includes but is not limited to the requirement of an observer to record the results which introduces examiner to examiner error as well as the unavoidable personal bias. In some instances, one of the personal biases may include in the assessment the player's importance to the team's success.

The environment where the diagnosis occurs may be important for accurate data collection. The recent tent environment may suffice, but in some cases a quiet area of a locker or examination room may be necessary, especially when the injury is obviously severe by clinical observation.

Other issues with the present concussion assessment tools may include the time it takes to administer. There may be the problem of uniform, unbiased data collection that may be done by instrumentation with minimal observer input. There may be not set uniform protocol that includes the necessity of a check list. There may be plurality of requirements to be included; mental processing speed, reaction time, and validity. The later to avoid "sandbagging" and/or malingering. It is important that there may be data on visual memory and verbal memory. The normative data and/or the patient's prior data may be present for immediate comparison. The data may be portable. The data may be the same as used in subsequent clinical setting. The test may produce sensitivity and specificity. The results based upon a sufficient data base may remove the necessity or human interpretation. The report may be transparent to the patient, his parents or guardian, and the athletic department.

The previously existing methods lack of means of uniform data collection, storage, or collection for later review. It may be recognized as important to include the patient's birth sex, family history, patient's mental wellness history, migraine and even their general intelligence or in the case of a student, their scholastic aptitude.

Furthermore, the volume of data available presently may be variable that a reasonable consensus has not been reached on what is important, the effect on return to play, rehabilitation, and prognosis. Finally, the test should have strong scientific foundation, yet be practical in implementation and interpretation.

Recognizing the complexity of the concussion it is understandable that there is a long felt need to accurately collect data requirements to address the assessment of concussion, diagnosis, treatment protocol, rehabilitation, and prognosis is still unmet.

Example 7: Dementia, Alzheimer, and Parkinson

Cognitive disorders that generally effect the aging population include dementia, Alzheimer's and Parkinson's disease, which may be related, but differ in etiology, diagnosis, treatment and prognosis. The previously existing method may not include present day means of prevention.

The previously existing methods may not include uniform assessment instrument that would properly differentiate and categorize each one. Each of these conditions may be complex, and the care of such a patient may vary with the magnitude of the condition, the prognosis, and finding a suitable environment for their care. In addition, these conditions may present a personal and family problems. Over time these conditions are producing a growing societal and humanitarian problem. There still may be need for early diagnosis and prognosis predictability for the patient and their life decisions. In addition, as science may advance there needs to be a means of accurately monitoring responses to various medications and or treatment regimens. The previously existing methods may be made after the fact when the clinical progression is obvious, which may have a need for early diagnosis when a treatment is discovered to prevent progression.

At present, a brain MRI is used in the diagnosis, but may not be necessarily definitive. It may not report functionality. The one or more tests for diagnosing cognitive conditions may include different parameters and variations for a young athlete who may have a concussion or an old subject who may have dementia.

Example 8: Diagnosing Cognitive Conditions

An example of diagnosing cognitive conditions is provided. In order to simulate cognitive conditions, alcohol imbibing will be used to create a certain cognitive impairment.

The first round of testing may be conducted when a subject does not consume any alcohol. Each test may be conducted multiple times to get an accurate baseline. For example, each test may be conducted 3 times to get an accurate baseline.

Subject may consume a certain amount of alcohol drinks so that a blood alcohol content (BAC) of the subject may reach a certain level, for example but not limited to, BAC=0.02%, 0.04%, 0.06%, and 0.08%. The alcohol drinks may include wines with alcohol content of approximately 13% by volume.

The second round of testing will be conducted after the BAC reaches the predetermined level and a waiting period. In one implementation, the waiting period may be 0 (i.e., there is no waiting period), or may be 10 minutes.

A preliminary question test is performed on the subject with BAC=0.09% and the subject's response is video recorded. A comparison between subject's response in the preliminary question test without and with the influence of alcohol show that verbal performance is significantly affected when the subject has cognitive conditions simulated by alcohol imbibing at BAC=0.09%. The effected performance may include difficulty in answering questions in fluid manner, noticeably slower speech, starring in space trying to answer one or more questions.

Figure 12A:
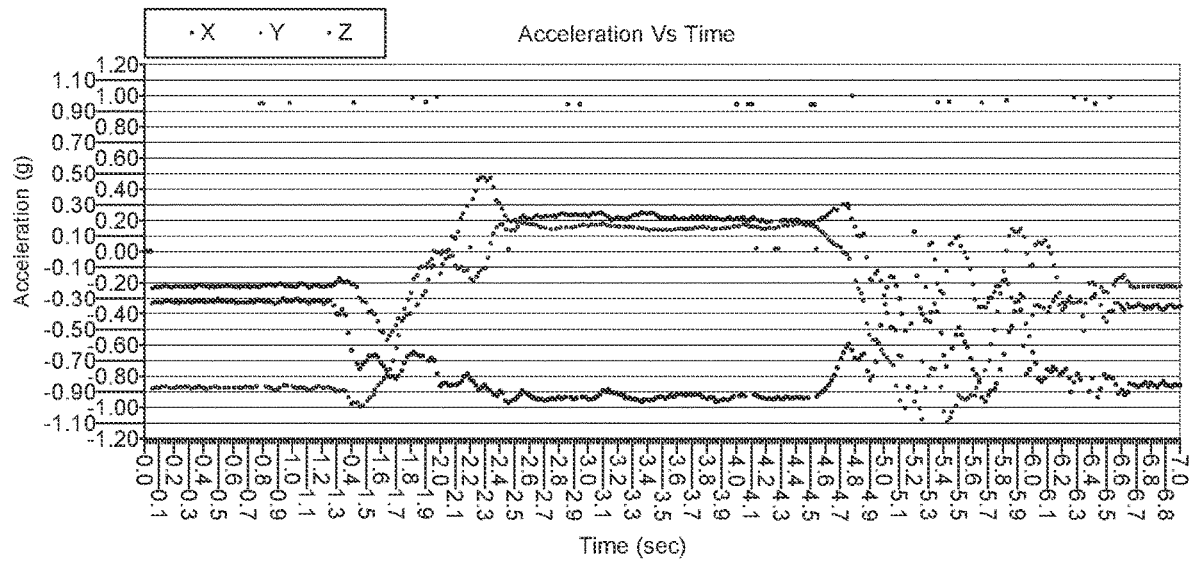
FIGS. 12A and 12B show a set of exemplary data collected by the system during "what time is it" test when a subject is under influence of alcohol.
Figure 12B:
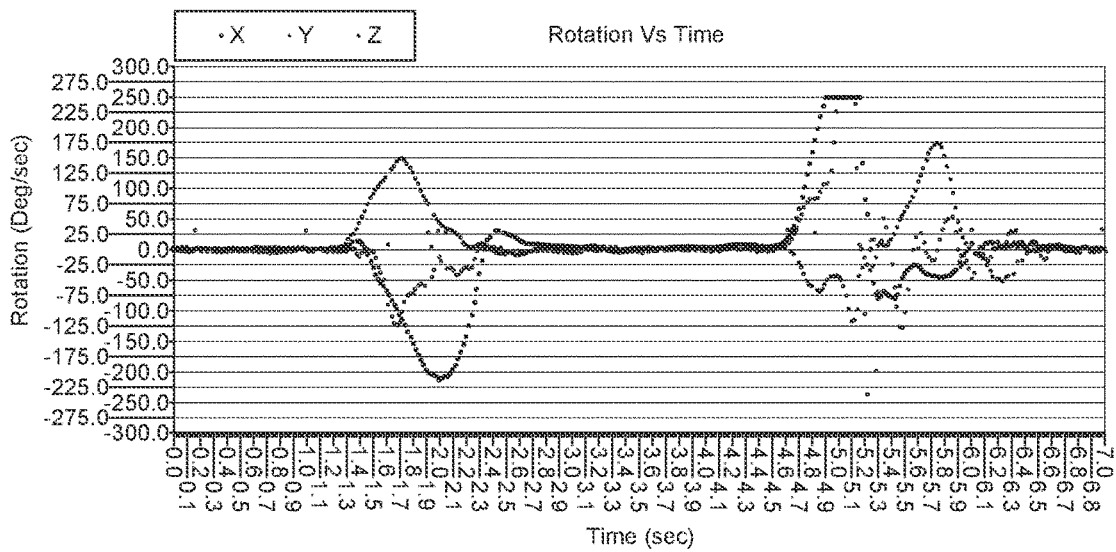

FIGS. 12A and 12B shows results of the MEMS sensor when a test of "what time is it?" is performed on the subject with BAC=0.09%.

Referring to FIG. 12A, a 3-dimensional acceleration data along x, y, and z axes may be obtained from an accelerometer MEMS sensor, which may be shown as a function of time in seconds.

Referring to FIG. 12B, a 3-dimensional rotation data around x, y, and z axes may be obtained from a gyroscope MEMS sensor, which may be shown as a function of time in seconds.

A comparison between FIGS. 8A-B and FIGS. 12A-B may show that it takes longer time for the subject to tell time when the subject has cognitive conditions simulated by alcohol imbibing at BAC=0.09%.

Figure 13A:
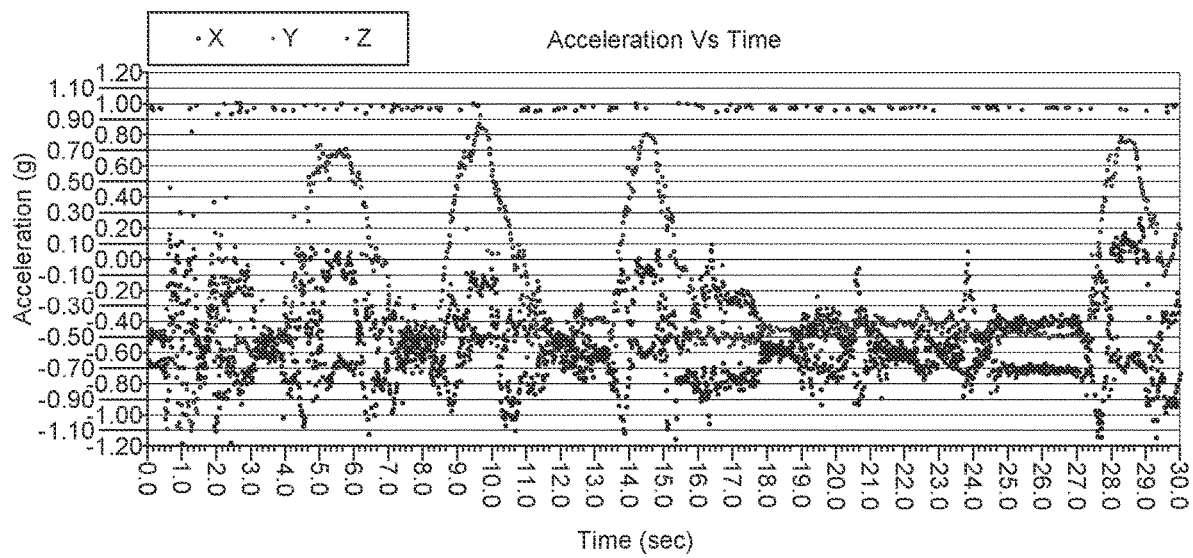
FIGS. 13A and 13B show a set of exemplary data collected by the system during "tactile edge orientation processing" test when a subject is under influence of alcohol.
Figure 13B:
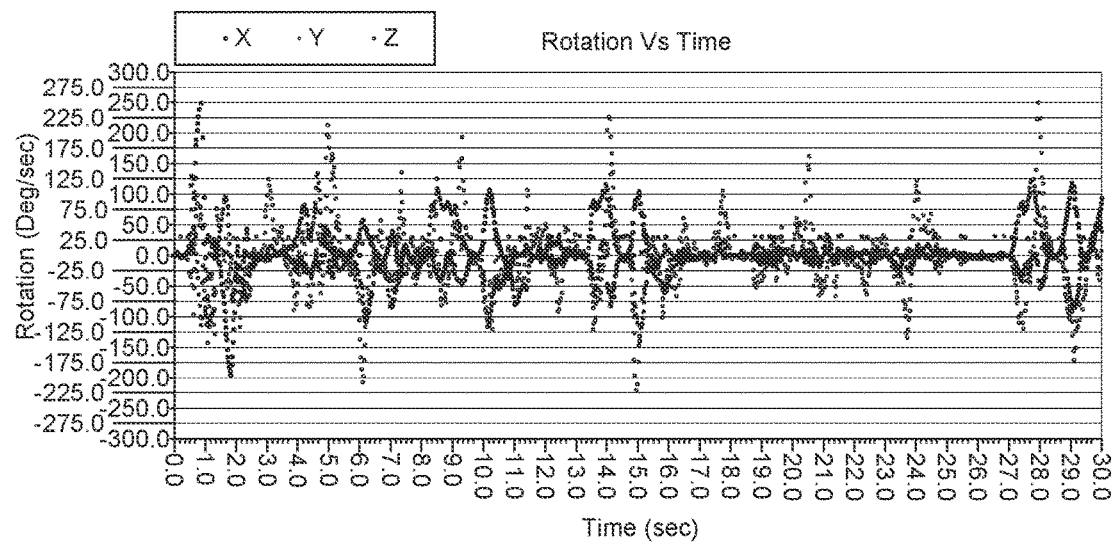

FIGS. 13A-B shows results of the MEMS sensor when a test of TEOP is performed on the subject with BAC=0.09%.

Referring to FIG. 13A, a 3-dimensional acceleration data along x, y, and z axes may be obtained from an accelerometer MEMS sensor, which may be shown as a function of time in seconds.

Referring to FIG. 13B, a 3-dimensional rotation data around x, y, and z axes may be obtained from a gyroscope MEMS sensor, which may be shown as a function of time in seconds.

A comparison between FIGS. 9A-B and FIGS. 13A-B may show that it takes longer time for the subject to fetch a certain item (e.g. a coin from a container) when the subject has cognitive conditions simulated by alcohol imbibing at BAC=0.09%.

Figure 14A:
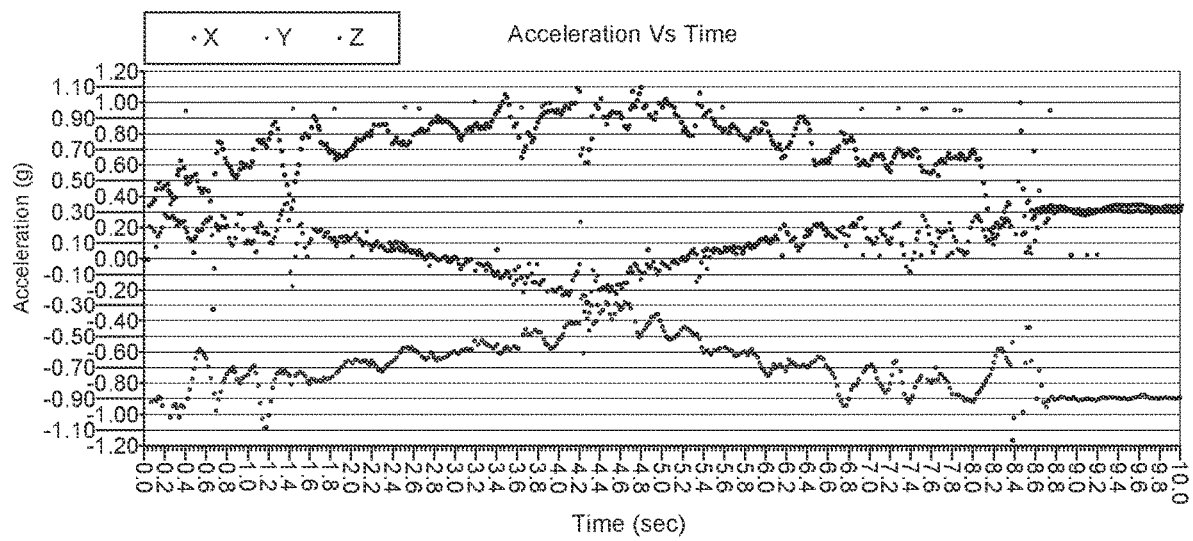
FIGS. 14A and 14B show a set of exemplary data collected by the system during "lower extremity leg movement" test when a subject is under influence of alcohol.
Figure 14B:
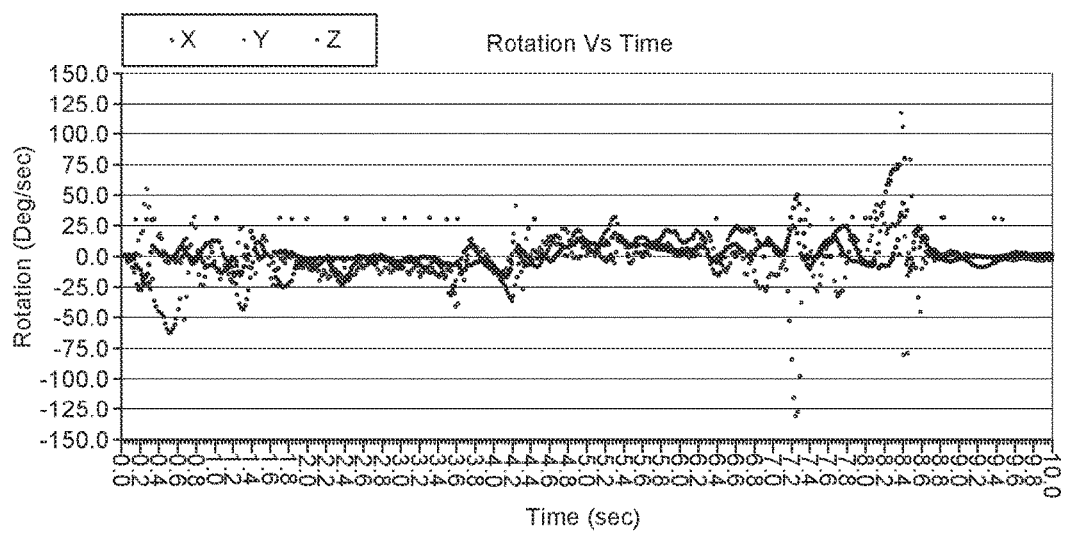

FIGS. 14A-B shows results of the MEMS sensor when a test of "lower extremity leg movement" is performed on the subject with BAC=0.09%.

Referring to FIG. 14A, a 3-dimensional acceleration data along x, y, and z axes may be obtained from an accelerometer MEMS sensor, which may be shown as a function of time in seconds.

Referring to FIG. 14B, a 3-dimensional rotation data around x, y, and z axes may be obtained from a gyroscope MEMS sensor, which may be shown as a function of time in seconds.

A comparison between FIGS. 11A-B and FIGS. 14A-B may show that motor impairment is visible when the subject has cognitive conditions simulated by alcohol imbibing at BAC=0.09%.

The present disclosure describes an embodiment with tests for diagnosing cognitive condition, supporting evidence in alcohol/drug driving arrests or in alcohol/drug abuse monitoring of subject caught with alcohol/drug additions. The present disclosure also describes an embodiment for diagnosing and providing treatment recommendations for subject with other drug additions, for example, but not limited to opium additions or even a certain type of prescription drugs.

In one implementation, the present disclosure describes an example of the above-described embodiment in identifying a malinger. When a patient claims to have a certain condition, the above-described embodiment may be used to confirm or refute the condition claimed by the patient. The above-described embodiment may be used to perform one or more tests and record results over an extended time, for example but not limited to, one or more repeated test once a day for a week, or one or more repeated test every other day for six times over twelve days.

In another implementation, the present disclosure describes an example of the above-described embodiment in identifying an intoxication. For one example, when a subject claims to have a certain degree of intoxication, the above-described embodiment may be used to confirm or refute the degree of the intoxication condition claimed by the subject. For another example, when a subject claims to have no intoxication, the above-described embodiment may be used to confirm or refute whether the subject is intoxicated.

Example 9: Upper Extremity; Dominant Hand (R/L)

A subject answers the following questions: Person? (correct/different/delayed); place? (correct/different/delayed) Time of year? (correct/different/delayed) Time of day? (correct/different/delayed).

2-point discrimination test: result in mm; Check location. Instructions given by examiner: check given instructions appear to be understood: (yes/no/repeated/cancelled test). Object to be retrieved: (coin, dice, marble, key, bullet, etc.)

While the invention has been described with reference to illustrative embodiments, this description is not meant to be limiting. Various modifications of the illustrative embodiments and additional embodiments of the disclosure will be apparent to one of ordinary skill in the art from this description. Those skilled in the art will readily recognize that these and various other modifications can be made to the exemplary embodiments, illustrated, and described herein, without departing from the spirit and scope of the present disclosure. It is therefore contemplated that the appended claims will cover any such modifications and alternate embodiments. Certain proportions within the illustrations may be exaggerated, while other proportions may be minimized. Accordingly, the disclosure and the figures are to be regarded as illustrative rather than restrictive.

The invention claimed is:

1. A method for diagnosing a cognitive disorder in a test subject comprising:

performing a tactile edge orientation processing test on the test subject;

measuring the test subject's tactile edge orientation processing test performance with a microelectromechanical sensor configured to record data comprising an accelerometer or a gyroscope, and a microprocessor configured to: producing a test subject motion signature or tracing with the microelectromechanical sensor from the tactile edge orientation processing test;

producing a normal motion signature or tracing with the microelectromechanical sensor from the tactile edge orientation processing test from one or more normal subject(s) with no cognitive disorder;

performing a cognitive disorder diagnosis on the test subject by comparing the normal motion signature or tracing with the test subject motion signature or tracing to determine whether a difference between the test subject's motion signature or tracing and the normal motion signature or tracing is larger than a cognitive disorder-specific threshold.

2. The method of claim 1, wherein the tactile edge orientation processing test comprises distinguishing between various shaped and sized objects.

3. The method of claim 1, wherein the tactile edge orientation processing test comprises a two-point discrimination test.

4. The method of claim 1, wherein the tactile edge orientation processing test comprises testing lower extremity coordination.

5. The method of claim 1, wherein the tactile edge orientation processing test comprises testing upper extremity coordination.

6. The method of claim 1, wherein the cognitive disorder comprises dementia, Alzheimer's, brain trauma, or concussion, attention-deficit/hyperactivity disorder (ADHD), autism, learning disabilities, intellectual disability, mental retardation, conduct disorders, cerebral palsy, or impairments in vision and hearing.

7. The method of claim 1, wherein the motion signature or tracing is a graphic motion signature.

8. The method of claim 1, wherein the motion signature or tracing comprises a path, a pattern, or a graphic record.

9. The method of claim 2, wherein the various shaped and/or sized objects comprise a coin, a key, or an instrument.

10. The method of claim 2, wherein the tactile edge orientation processing test comprises reaching in a bag and selecting a predetermined object.

11. The method of claim 4, wherein the tactile edge orientation processing test comprises instructing the test subject to run a heel up and down an anterior contralateral leg.

12. The method of claim 1, wherein the data recorded from the microelectromechanical sensor is saved in a paper format, a video format, an audio format, a text digital format, or a binary digital format.

* * * * *